United States Patent [19]
Houghten

[11] Patent Number: 4,758,655
[45] Date of Patent: Jul. 19, 1988

[54] SYNTHETIC POLYPEPTIDE CORRESPONDING TO A PORTION OF THE HEAT-LABILE ENTEROTOXIN OF *ESCHERICHIA COLI*, COMPOSITIONS AND METHODS OF THEREWITH

[75] Inventor: Richard A. Houghten, Solana Beach, Calif.

[73] Assignee: Scripps Clinic and Research Foundation, La Jolla, Calif.

[21] Appl. No.: 71,606

[22] Filed: Jul. 9, 1987

Related U.S. Application Data

[63] Continuation of Ser. No. 760,753, filed as PCT US84/02030 on Dec. 12, 1984, published as WO85/02611 on June 20, 1985, abandoned, which is a continuation-in-part of Ser. No. 559,469, Dec. 12, 1983, which is a continuation-in-part of Ser. No. 455,265, Jan. 3, 1983, Pat. No. 4,545,931.

[51] Int. Cl.[4] .......................... C07K 7/06; C07K 7/08; C07K 7/10

[52] U.S. Cl. .................................... 530/324; 530/325; 530/326; 530/327; 530/328

[58] Field of Search ............... 530/324, 325, 326, 327, 530/328

[56] References Cited

U.S. PATENT DOCUMENTS

| | | | |
|---|---|---|---|
| 4,314,993 | 2/1982 | Wijnendaele | 424/88 |
| 4,411,888 | 10/1983 | Klipstein et al. | 424/88 |
| 4,454,116 | 6/1984 | Brinton | 424/88 |
| 4,465,665 | 8/1984 | Dorescu | 424/92 |

OTHER PUBLICATIONS

Medical Hypothese, 5, 347-349, (1979).
Stimulus-Secretion Coupling in the Gastrointestinal Tract, 10, 108-109.
Infection and Immunity, (1983), 269-275, 42.
Journal of Bacteriology, Aug. 1983, vol. 155, pp. 728-733.
Biochemical and Biophysical Res. Commun., 320-325, (1983), vol. 112.
Infection and Immunity, (1982), 550-557, vol. 37.
Infection and Immunity, (1980), 91-97, vol. 29.
The Journal of Biological Chemistry, vol. 256, 7744-7746, (1981).
Proc. Nat'l Acad. Sci., 77, (1980), 4011-4015.

*Primary Examiner*—Delbert R. Phillips
*Attorney, Agent, or Firm*—Dressler, Goldsmith, Shore, Sutker & Milnamow, Ltd.

[57] ABSTRACT

Synthetic polypeptides containing about 10 to about 35 amino acid residues corresponding in sequence to the amino acid residue sequence of about position 35 to about position 95 from the amino-terminus of the B-subunit of the heat-labile enterotoxin of *Escherichia coli* are disclosed along with composite polypeptides containing the polypeptide sequence of the heat-stable *Escherichia coli* enterotoxin, as are polymers containing the synthetic polypeptide and composite polypeptide as repeating units. The polypeptides are useful as conjugates coupled to a carrier or as a polymer as the active ingredient of an inoculum to raise antibodies and for protecting an animal host against infection by heat-labile enterotoxin-producing bacteria.

19 Claims, 5 Drawing Sheets

FIG. 1

*E. coli* LT B-SUBUNIT

10
$LT_p$ met-asn-lys-val-lys-cys-tyr-val-leu-phe-thr-ala-leu-leu-ser-ser-leu-tyr -
$LT_h$ - - - - - - - - - - - - - - - - - cys -

20 30
$LT_p$ ala-his-gly / ALA-PRO-GLN-THR-ILE-THR-GLU-LEU-CYS-SER-GLU-TYR-ARG-
$LT_h$ - tyr - - - - SER - - - - - - - - - -

40 50
$LT_p$ ASN-THR-GLN-ILE-TYR-THR-ILE-ASN-ASP-LYS-ILE-LEU-SER-TYR-THR-GLU -
$LT_h$ - - - - - - - - - - - - - - - -

60
$LT_p$ SER-MET-ALA-GLY-LYS-ARG-GLU-MET-VAL-ILE-ILE-THR-PHE-MET-SER-GLY-
$LT_h$ - - - - - - - - - - - - - LYS - -

70 80
$LT_p$ GLU-THR-PHE-GLN - VAL-GLU-VAL-PRO-GLY-SER-GLN-HIS-ILE-ASP -SER-GLN-
$LT_h$ ALA - - - - - - - - - - - - - - -

90
$LT_p$ LYS-LYS-ALA-ILE-GLU-ARG-MET-LYS-ASP-THR-LEU-ARG-ILE-THR-TYR-LEU-
$LT_h$ - - - - - - - - - - - - - - -

100 110
$LT_p$ THR-GLU-THR-LYS-ILE-ASP-LYS-LEU-CYS-VAL-TRP-ASN-ASN-LYS-THR-PRO-
$LT_h$ - - - - - - - - - - - - - - - -

120 124
$LT_p$ ASN-SER-ILE-ALA-ALA-ILE -SER-MET-LYS-ASN
$LT_h$ - - - - - - - - GLU -

PROTECTION IN RATS IMMUNIZED WITH $B_{FRAG}$-ST VACCINE GIVEN EXCLUSIVELY BY THE PERORAL ROUTE

SYNTHETIC POLYPEPTIDE CORRESPONDING TO A PORTION OF THE HEAT-LABILE ENTEROTOXIN OF *ESCHERICHIA COLI*, COMPOSITIONS AND METHODS OF THEREWITH

DESCRIPTION

CROSS-REFERENCE TO RELATED APPLICATION

This application is a continuaton of application Ser. No. 760,753, filed as PCT US84/020 on Dec. 12, 1984, published as WO85/02611 on Jun. 20, 1985, now abandoned, which is a continuation-in-part of copending application Ser. No. 559,469, filed Dec. 12, 1983, which is a continuation-in-part of copending application Ser. No. 455,265, filed Jan. 3, 1983.

BACKGROUND ART

Acute diarrheal disease due to transient colonization of the small bowel by enterotoxigenic strains of *Escherichia coli* (*E. coli* or ETEC) is a major health problem of global scope for both humans and for animal husbandry. These organisms, together with rotavirus and *Campylobacter jejuni* (*C. jejuni*), are the principal cause of the often fatal acute diarrhea that is common among infants living in underdeveloped countries and among neonatal animals, particularly lambs and piglets. ETEC strains are also the usual cause of acute diarrhea among persons from temperate zones who travel to the tropics, and may be responsible for sporadic or epidemic episodes of diarrhea among children and adults living in either temperate or tropical areas.

The disease caused by ETEC is mediated by the release of two enterotoxins, either singly or together. The low molecular weight, heat-stable toxin (ST) produced by ETEC strains of human or porcine origin has recently been-purified. Preparations of ST have a relatively high content of half-cystine, cause secretion by stimulating guanylate cyclase and are haptenic as evidenced by their capacity to raise an antitoxin response in animals immunized with the toxin coupled to a large molecular weight carrier.

The large molecular weight, antigenic heat-labile toxin (LT) has been purified to homogenicity. Its subunit structure has been characterized as (1) five B-subunits that attach the holotoxin (complete toxin) to specific $GM_1$ ganglioside receptors on the mucosal surface, and (2) a single A-subunit that stimulates intracellular adenylate cyclase activity, thus evoking fluid and electrolyte secretion.

Immunization with either the biologic LT, the biologic LT B-subunit or the biologic ST toxin induces an antitoxin response in experimental animals that protects against homologous and heterlogous serotypes of strains that produce the specific toxin used for immunization. Thus, immunization with LT whole toxin or its B-subunit yields protection against viable heterlogous strains that produce this toxin alone ($LT^+/ST^-$) or together with ST ($LT^+/ST^+$), but not against those which make just ST($LT^-/ST^+$). Similarly, immunization with biologic ST provides protection against direct challenge with viable heterlogous ST-producing strains (($LT^-/ST^+$ and $LT^+/ST^+$), but not against LT-producing strains.

However, the biologic toxins or the B-subunit are not suitable for immunization when given alone in view of their toxicity, their failure to provide protection against strains that produce the other toxin form, and the fact that the large molecular weight carriers that have been used to render the haptenic biologic ST molecule immunogenic are typically unsuitable for human use. Therefore, the most practical approach for the prevention of ETEC-induced diarrhea would be an immunization program that provides protection against heterologous ETEC serotypes that produce either or both of the LT or ST enterotoxins and does not use an irrelevant carrier molecule.

U.S. Pat. No. 4,411,888 to Klipstein and Klipstein et al., *J. Infec. Dis.* 147:318–326 (1983) report, inter alia, the development of a vaccine made by conjugating natural or synthetic ST toxin to the biologic B-subunit of LT toxin (LTB) by means of the carbodiimide reaction. As a result of that reaction, synthetic ST acquires immunogenicity when coupled to the large molecular weight LTB carrier, the LTB maintains most of its immunogenicity, while both cross-linked materials lose most of their toxic (secretion-inducing) properties. Rats immunized with the vaccine so produced were reported to be strongly protected against challenge with either LT or biologic ST, as well as against challenge with viable ETEC strains that produce those toxins.

The LTB preparation used for that vaccine was obtained via recombinant methods. That method of preparation, while producing a useful result, is relatively expensive since the resulting recombinant LTB must be purified extensively to remove toxic materials before it can be formulated into a useful vaccinating agent in combination with ST. Recombinant LTB must also be coupled to ST with a covalent linking agent such as soluble carbodiimide, gluteraldehyde, or dimethylsuberimidate, which may not be acceptable in the final formulation for human use. Finally, the size of LTB may necessitate the use of an excess of ST in the preparation of the LT/ST immunogen formulation, which increases costs accordingly.

Richard A. Lerner and co-workers, have shown that a synthetic polypeptide whose amino acid residue sequence corresponds to that of a portion of a protein may be used to elicit antibodies that recognize the intact protein. See Sutcliffe et al. *Science* 219:660–666 (1984), for a review. Synthetic polypeptides designed following the initial work of Lerner et al. have been successfully used for the preparation of the synthetic ST molecule described before.

The nucleotide sequences coding for the LTB proteins from human- and porcine-infecting ($LT_h$ and $LT_p$, respectively) *E. coli* have been determined. Translation of the nucleotide sequences into amino acid sequences leads to proteins whose largest form could contain 124 amino acid residues. See Dallas and Falkow, *Nature* 288:499–501 (1980) and Yamamoto et al., *J. Bacteriol.* 155:728–733 (1983).

The 124 residue protein includes 21 amino acid residues at the amino-terminus in what is sometimes referred to as a "signal peptide". Reported amino acid residue position numbers of LTB in the literature consequently may differ by 21 positions, depending upon whether the authors whose work is reported include or exclude the 21 residue signal peptide in their position numbering nomenclature.

BRIEF SUMMARY OF THE INVENTION

The present invention has several aspects. One aspect contemplates a synthetic polypeptide containing about 10 to about 35 amino acid residues that correspond in sequence to the amino acid residue sequence of about position 35 to about position 95 from the amino-terminus of the B-subunit of the heat-labile enterotoxin of *Escherichia coli* (LTB); the position numbers including the 21 residue signal polypeptide of the B-subunit. In particularly preferred practice, a synthetic polypeptide contains about 15 to about 30 residues corresponding in sequence to about position 55 to about position 85 from the amino-terminus of the B-subunit, again wherein the position numbers include the 21 residue signal polypeptide. Most preferably, the synthetic polypeptides contain about 20 to about 25 amino acid residues that correspond in sequence to about position 60 to about position 85 from the amino-terminus of the B-subunit of the heat-labile enterotoxin, again including the 21 residue signal polypeptide of that subunit.

Another aspect of this invention contemplates a composite LT/ST polypeptide containing about 25 to about 55 amino acid residues that comprises to 2 amino acid residue sequences peptide bonded together. One of those amino acid residue sequences corresponds in sequence to at least the carboxy-terminal 14 residues of the heat-stable enterotoxin *Escherichia coli* (ST), while the second sequence corresponds to positions about 35 to about 95 from the amino-terminus of the B-subunit of the heat-labile enterotoxin of *Escherichia coli* (LTB), wherein the latter position numbers include the 21 residue signal polypeptide with the B-subunit.

In preferred practice, the first named amino acid residue sequence portion of this polypeptide includes the 18 residue sequence of the heat-stable enterotoxin of *E. coli* and the before-described more preferred sequence that corresponds to a portion of the B-subunit of the heat-labile enterotoxin of *E. coli*. Most preferably, the polypeptide contemplated includes the 18 residue sequence of the heat-stable enterotoxin and the before-described about 20 to about 25 residue sequence corresponding to a portion of the B-subunit of *E. coli* heat-labile enterotoxin. The two sequences constituting a composite LT/ST polypeptide are preferably bonded together by a peptide bond between the carboxy-terminal residue of one sequence and the amino-terminal residue of the other sequence.

The above polypeptide, referred to herein as a composite LT/ST polypeptide, may also include 1 to about 4 additional amino acid residues linked to one or both terminii, as well as 1 to about 2 additional amino acid residues between the two polypeptide sequences that constitute the composite. Each of those additional residues bears an acidic or basic side chain that is capable of bearing an ionic charge at the pH of the jejunum (about pH 6.5). When more than one of those additional residues is present, each of the side chains of an additional amino acid residue is capable of bearing the same ionic charge at the jejunum pH value. Preferred additional amino acid residues that may be linked to either or both of the terminii and between the constituent polypeptides are selected from the group consisting of lysine (Lys) and arginine (Arg) residues, or are selected from the group consisting of aspartic acid (Asp) and glutamic acid (Glu) residues.

A composite LT/ST polypeptide of this embodiment of the invention may be also described generally, written from left to right and in the direction from amino-terminus to carboxy-terminus, as a compound corresponding to the formula:

$$(X)_n\text{-}(A)_o\text{-}(Z)_r\text{-}B\text{-}(Z)_s\text{-}(A)_p\text{-}(Y)_m$$

wherein:

X, Y, and Z, when present, are additional amino acid residues to the sequences that are
- (a) selected from the group consisting of Lys and Arg residues, or
- (b) selected from the group consisting of Asp and Glu residues;

"n" and "m" are integers having a value of zero, 1, 2, 3 or 4, such that the respective X and Y are absent when either or both of "n" and "m" have a value of zero, while the respective X and Y residues are present when either or both of "n" and "m" have a value of other than zero, with the average number of X and Y residues present per polypeptide being equal to the values of X and Y, respectively;

"r" and "s" are integers having a value of zero, 1 or 2, such that the respective Z is absent when either or both of "r" and "s" have a value of zero, while the respective Z is present when "r" and "s" are present, the average number of Z residues per composite LT/ST polypeptide molecule or repeating unit being equal to the value of "r" or "s", with the proviso that when either of "r" or "s" is greater than zero, the other of "r" or "s" is zero and the respective Z whose "r" or "s" is zero is absent;

"o" and "p" are integers having the value of zero or 1 so that the corresponding A is absent when either of "o" and "p" have a value of zero, with the proviso that "o" and "p" may not both have the same value;

A is a polypeptide containing about 10 to about 35 amino acid residues corresponding in sequence to the amino acid residue sequence of about position 35 to about position 95 from the amino-terminus of the B-subunit of the heat-labile enterotoxin of *Escherichia coli*, wherein the position numbers include the 21 residue signal polypeptide of the B-subunit; and B is a polypeptide containing up to 18 amino acid residues corresponding in sequence to at least the carboxy-terminal 14 residues of the heat-stable enterotoxin of *Escherichia coli*.

Also contemplated in this invention are polymers that include a plurality of polypeptide repeating units that contain about 10 to about 35 amino acid residues corresponding in sequence to the amino acid residue sequence of about position 35 to about position 95 from the amino-terminus of the B-subunit of the heat-stable enterotoxin of *Escherichia coli*, wherein the position numbers include the 21 residue signal peptide of the B-subunit. These polymers, when dissolved or dispersed in a physiologically tolerable diluent as an inoculum, and introduced in an effective amount into a host mammal are capable of inducing the production of antibodies that immunoreact with the native enterotoxin B-subunit.

In one embodiment, the repeating units of the polymer of this invention are bonded together by cystine disulfide bonds formed by oxidation of Cys residues added to the repeating unit terminii; the Cys residues being present at both the amino-terminus and carboxy-terminus of the repeating unit polypeptides prior to oxidation. Such repeating units, in the unoxidized form, are referred to as diCys-LT polypeptides. The polymer is a linear homopolymer when no other monomeric repeating units are present during the polymer-forming oxidation.

A random three-dimensional network copolymer results when oxidative polymerization is carried out using both the above diCys-LT polypeptide and a second polypeptide repeating unit whose amino acid residue sequence corresponds to at least the 14 carboxy-terminal amino acid residues of the *E. coli* heat-stable enterotoxin (ST polypeptide) discussed hereinbefore. Where network polymers are desired, at least three, and most preferably all six Cys residues of the ST polypeptide are present. It is also preferred that a complete, 18 residue ST polypeptide sequence be utilized.

A network polymer that comprises a plurality of composite LT/ST polypeptide repeating units is contemplated in a still further aspect of the polymers of this invention. The polypeptide repeating units, written from left to right and in the direction from amino-terminus to carboxy-terminus, individually correspond to the formula of the before-described composite LT/ST polypeptide. The repeating units of a particularly preferred network polymer, written from left to right and in the direction from amino-terminus to carboxy-terminus, individually correspond to the formula:

$(X)_n$MetValIleIleThrPheMet(Lys)SerGlyGlu
(Ala)ThrPheGlnValGluValProGlySerGln-
HisIleAspSerGlnLys
AsnThrPheTyrCysCysGluLeuCysCysTyr(Asn)
ProAlaCysAlaGlyCysAsn(Tyr)$(Y)_m$ wherein X and Y, when present, are amino acid residues that are
- (a) selected from the group consisting of Lys and Arg residues, or
- (b) selected from the group consisting of Asp and Glu residues; and "n" and "m" are integers having the value of zero, 1, 2, 3 or 4, such that the respective X and Y are absent, when either or both of "n" and "m" have a value of zero, while the respective X and Y residues are present when either or both of "n" and "m" have a value of other than zero, with the average number of X and Y residues present per polypeptide repeating unit being equal to the values of X and Y, respectively;

the amino acid residues in parentheses are each an alternative to the immediately preceding amino acid residue in the sequence of the formula; and the repeating units are bonded together by intramolecular, interpolypeptide cystine bonds formed between oxidized Cys residues of the repeating units.

Also contemplated in this invention are inocula useful for raising antibodies to be utilized in diagnostic methods and systems, or as vaccines capable of protecting animals including humans from the heat-labile, or heat-labile and heat-stable endotoxins of *E. coli.* The inocula contain an effective amount of an LTB polypeptide conjugate, composite LT/ST polypeptide conjugate or network polymer as described herein in a physiologically tolerable diluent. The inocula when introduced in a unit dose into a host mammal as by injection or orally is capable of inducing the production of antibodies that immunoreact with at least the B-subunit of the heat-labile enterotoxin of *E. coli.* In more preferred practice, the antibodies so induced immunoreact with both the B-subunit of the heat-labile enterotoxin and also with the heat-stable enterotoxin of *E. coli.* Such an inoculum when used as a vaccine to immunize a host animal such as a human, swine or a laboratory animal such as a rat, protects the host from heat-labile enterotoxin-producing *E. coli,* and more preferably also from heat-stable enterotoxin-producing *E. coli.*

BRIEF DESCRIPTION OF THE DRAWINGS

In the drawings forming a portion of this description:

FIG. 1 shows the translated amino acid residue sequences of the B-subunit of the porcine ($LT_p$) and human ($LT_h$) heat-labile enterotoxins of *Escherichia coli* written from left to right and in the direction from amino-terminus to acid residues are depicted by hyphens. The amino acid residues of the 21-residue signal peptide sequence are shown in lower case letters, while the residues of the major portion of the protein are shown in capital letters. A virgule (/) separates the signal peptide sequence from the remaining sequence. Dashes in the $LT_h$ sequence (beneath the $LT_p$ sequence) indicate that the identical residue is present in both sequences. Residues that differ between the sequences are indicated. Numerals above the $LT_p$ sequence indicate residue positions measured from the amino-terminus. The sequences were reported by Dallas and Falkow, *Nature* 288:499–501 (1980) and by Yamamoto et al., *J. Bacteriol.* 152:506–509 (1982) and Yamamoto et al., *J. Bacteriol.* 155:728–733 (1983).

Figure 2:
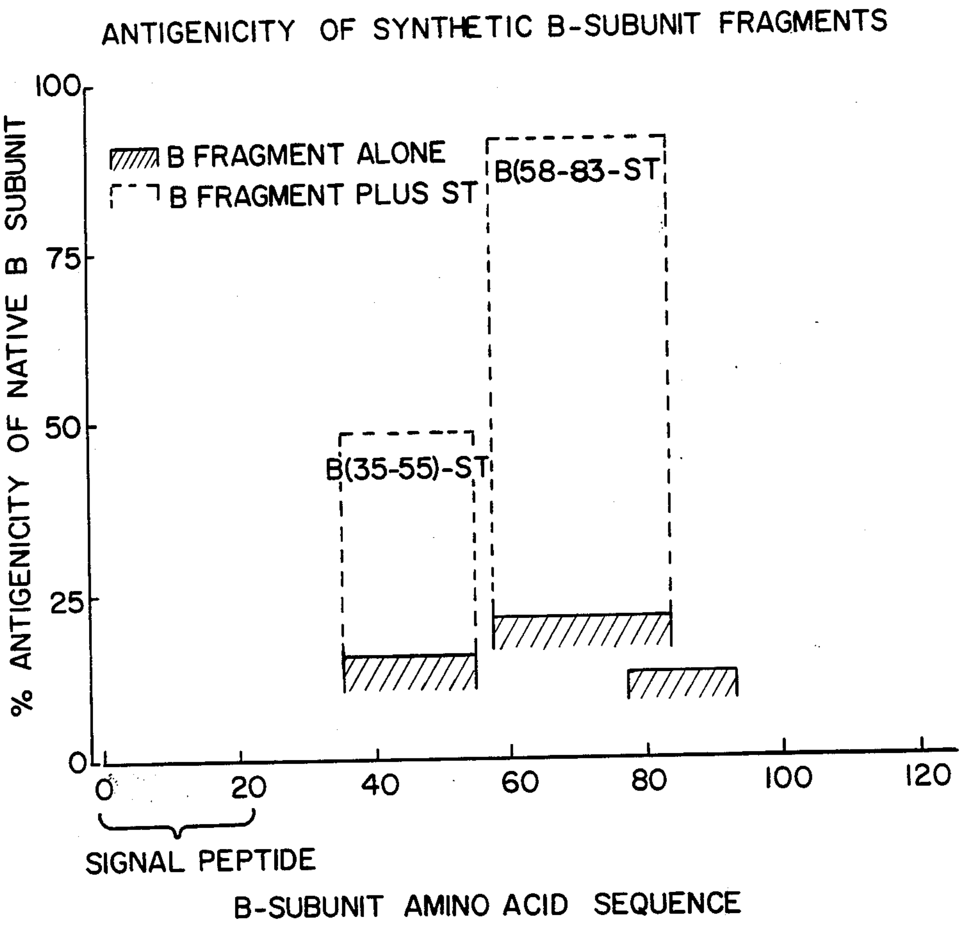
FIG. 2 is a graph showing the antigenicities of three of the $LT_p$-related polypeptides studied as measured by the B/B ELISA technique described in the MATERIALS AND METHODS Section, and are expressed as a percentage of the antigenicity of the native $LT_h$ B-subunit. The ordinate is in percentage of native $LT_h$ B-subunit antigenicity. The abscissa illustrates sequence position on the $LT_p$ B-subunit protein. Antigenicities of the $LT_p$ B-related polypeptides alone are shown by rectangles enclosing diagonal lined hatchings; the thickness of the enclosed hatchings is for purposes of easy reading, and not to express experimental error in the measurements. Antigenicities of the $LT_p$ B-related polypeptides peptide bonded to the amino-terminal residue of an ST Ibh polypeptide and oxidatively polymerized are illustrated by dashed-line rectangular enclosures.

The present invention provides several benefits and advantages. One benefit of this invention is that it provides a unitary, totally synthetic vaccine against both heat-labile and heat-stable enterotoxin-producing strains of *Escherichia coli.*

Another benefit is that the unitary vaccine induces substantially no intestinal secretion in the immunized host; i.e., the vaccines made in accordance with this invention have substantially none of the detrimental secretion-inducing activity of either enterotoxin.

One advantage of this invention is that its LT B-subunit-related polypeptides are prepared synthetically by standard laboratory synthetic procedures, and are thereby free from the presence of undesirable biologic contaminants.

A further advantage of the present invention is that its polypeptides are relatively inexpensive to prepare and purify as compared to biologically or recombinant DNA technology.

Still further benefits and advantages will be apparent to those skilled in the art from the detailed description that follows.

DETAILED DESCRIPTION OF THE INVENTION

The present invention contemplates a synthetic polypeptide containing about 10 to about 35 amino acid residues corresponding in sequence to about position 35 to about position 95 from the amino-terminus of the B-subunit of the heat-labile enterotoxin *Escherichia coli,* wherein the position numbers include the 21 residue signal peptide of the B-subunit. Conjugates, composite LT/ST polypeptides, and polymers that include such polypeptides, as well as inocula that include an effective amount of a, conjugated polypeptide, composite LT/ST polypeptide or polymer, antibodies induced by the inocula and methods related thereto are also contemplated.

I. LTB POLYPEPTIDES

The translated amino acid residue sequences of the B-subunit of $LT_p$ and $LT_h$ are shown in FIG. 1. The amino acid residue sequence of the B-subunit of the heat-labile enterotoxin of *Escherichia coli* from the sequence position numbered 35 to sequence position numbered 95 (wherein the position numbers include the 21 residue signal polypeptide) written as a single sequence, from left to right in the direction from amino-terminus to carboxy-terminus, is represented by Formula I, below:

FORMULA I

```
35               40                  45
AsnThrGlnIleTyrThrIleAsnAspLysIleLeuSerTyrThr

50             55              60                  65
GluSerMetAlaGlyLysArgGluMetValIleIleThrPheMet(Lys)Ser

                 70                75                80
GlyGlu(Ala)ThrPheGlnValGluValProGlySerGlnHisIleAspSer

           85                90             95
GlnLysLysAlaIleGluArgMetLysAspThrLeuArgIle
```

wherein the parenthesized amino acid residues are alternatives to the immediately preceding residue, respectively, in the sequence of the formula; i.e., the residue to the left of each parenthesized residue. The numerals above particular residues indicate the amino acid positions in the sequence, measured from the amino-terminus, and including the signal peptide sequence.

It is noted that the sequence of Formula I contains two alternative amino acid residues. Those residues are located at positions 64 and 67 from the amino-terminus. Unless otherwise indicated, reference herein to a polypetpide of this invention that includes an amino acid residue sequence corresponding to a portion of LTB (an LTB polypeptide) is meant to include both the $LT_h$ and $LT_p$ polypeptide sequences as a composite sequence; i.e., an amino acid residue sequence that includes (a) either a Lys or a Met residues at position 64, and (b) eiher a Glu residue or an Ala residue at position 67. Thus, an LTB polypeptide that may include the four sequences shown below from positions 64 through 67 is implied by reference to an LTB polypeptide or by reference to LTB:

(A) MetSerGlyGlu
(B) LysSerGlyGlu
(C) MetSerGlyAla
(D) LysSerGlyAla.

The data discussed hereinafter illustrate that a synthetic polypeptide containing about 10 to about 35 amino acid residues that correspond in sequence to positions 35 to about 95 of the B-subunit of the heat-labile enterotoxin (LTB) is useful as an immunogen for inducing the production of antibodies that may be used in diagnostics for the presence of the heat-labile enterotoxin (LT) produced by *E. coli.* More preferably, the polypeptides of the present invention are utilized as an immunogen in inocula. In those uses, it is preferred that the polypeptides contain about 15 to about 30 amino acid residues and that the sequence of the polypeptides correspond to the LTB sequence of position about 55 to about position 85. Most preferably, a polypeptide containing about 20 to about 25 residue is utilized, and the sequence of that polypeptide corresponds to the sequence of about position 60 to about position 85 of LTB. A polypeptide so utilized is typically used as a conjugate of the polypeptide coupled to a carrier. Unconjugated polypeptides are also useful in diagnostics as an antigen or competing ligand for anti-LTB polypeptide or anti-native LT antibodies.

II. COMPOSITE LT/ST POLYPEPTIDES INCLUDING LTB SEQUENCES

A particularly useful embodiment of this invention is a composite polypeptide that contains about 25 to about 55 amino acid residues and is comprised of two amino acid residue sequences bonded together by a peptide bond between the carboxy-terminal residue of the first sequence and the amino-terminal residue of the second sequence. The two amino acid residue sequences of the composite polypeptide include a synthetic polypeptide described hereinbefore whose amino acid residue sequence corresponds to positions about 35 to about 95 from the amino terminus of LTB. The second sequence corresponds to at least the carboxy-terminal 14 amino acid residues of the heat-stable enterotoxin of *Escherichia coli* (hereinafter generally referred to as ST). Such a polypeptide is referred to hereinafter as a composite LT/ST polypeptide.

The peptide bond between the two amino acid residue sequences that constitute the composite LT/ST polypeptide may be formed between the amino-terminal residue of an ST sequence and the carboxy-terminal residue of the LTB sequence, or between the amino-terminal residue of the LTB sequence and the carboxy-terminal residue of the ST sequence. The polypeptide sequences that constitute a composite LT/ST polypeptide may also be referred as being bonded head-to-tail.

It is particularly preferred that the amino acid sequence corresponding to the heat-stable (ST) portion of the composite LT/ST polypeptide include the 18 residue (18-mer) sequence of the ST molecule.

At least two types of ST have been identified by their physical properties. The first type known as ST I (also referred to as STa) is soluble in methanol and is active in the suckling mouse model. The second type, ST II (also referred to as STb) is methanol insoluble and not active in the suckling mouse model, but is active in ligated pig ileal loops. The ST I polypeptides are of interest herein and will be the only ST polypeptide type referred to herein.

Among the ST I polypeptides, at least two similar polypeptides, or determinant domains of those polypeptides, have been identified, and their amino acid residue sequences have determined. These two types of ST I are referred herein as (i) ST Ia which was initially found in a bovine *E. coli* strain and a portion of which is also encoded in porcine strains, and (ii) that designated ST Ib from a human isolate of *E. coli.*

The nucleotide sequence coding for the ST Ia polypeptide has been determined. Translation of the nucleotide sequence into a polypeptide amino acid sequence leads to a polypeptide that contains 72 amino acids capped at the carboxy-terminus with a tyrosine group [So et al., *Proc. Natl. Acad. Sci. USA,* 77:4011–4015 (1980)]. The ST Ib polypeptide is reported to contain only 18 amino acids [Chan et al., *J. Biol. Chem.* 256:7744–7746 (1981)], and those 18 residues are homologus with the 18 carboxy-terminal residues encoded by the ST Ia nucleotide sequence.

Recent evidence indicates that the originally reported amino acid residue sequence for ST Ib was in error. The originally reported carboxy-terminal asparigine (Asn) residue is now believed to be a tyrosine (Tyr) residue, while the originally reported Tyr at position 11 from the amino-terminus of the 18-mer is now believed to be an Asn residue. For ease of discussion, polypeptides whose sequences correspond to the original sequence reported by Chan et al., supra, will be referred to herein as ST Ibh, while polypeptides corresponding to the revised sequence will be referred to as ST Ibp.

The 18 amino acids of the ST Ibh polypeptide (18-mer) show great homology to amino acids numbered 55 through 72 for the polypeptide of ST Ia. The homologous, almost identical, region of ST Ibh is illustrated hereinbelow along with the reported sequence for ST Ia and that of ST Ibp, beginning at amino acid number 55, from left to right and in the direction of amino-terminus to carboxy-terminus, of the ST Ia polypeptide:

ST Ia: AsnThrPheTyrCysCysGluLeuCysCys
ST Ibh: AsnThrPheTyrCysCysGluLeuCysCys
ST Ibp AsnThrPheTyrCysCysGluLeuCysCys
AsnProAlaCysAlaGlyCysTyr
TyrProAlaCysAlaGlyCysAsn
AsnProAlaCysAlaGlyCysTyr

As can be seen, the 18 residue sequences of ST Ia and ST Ibp are identical.

Examination of the above three (two different) 18 amino acid residue polypeptide sequences also reveals that six half-cystine (Cys) residues that are present. Oxidation of those half-cystine residues to cystine residues containing intramolecular, intrapolypeptide disulfide bonds in the native enterotoxin is thought to lend the observed heat stability to that material.

It is further noted, however, that while cystine disulfide bonds are known to be present in native ST, it is not known which pairs of half-cystine residues combine to form the three disulfide bonds that are present in the native ST molecule. Those three disulfide bonds can theoretically be formed from fifteen different combinations of the six Cys residues present.

Staples et al., *J. Biol. Chem.* 255:4716–4721 (1980) have shown that the disulfide linkages of biologic ST are required for biological activity of the toxin. Thus, chemical reduction to form half-cystines or performic acid oxidation to cysteic acid was shown to destroy the biological activity of the toxin. In addition, Chan et al., supra, have reported that the first four residues from the amino-terminus of the homologous 18-amino acids of the above sequence of ST Ibh are not required for biological activity. Thus, biological activity was obtained from the amino acid-containing polypeptide comprising the above carboxy-terminal 14 amino acids and their disulfide bonds.

Aimoto et al., *Biochem. Biophys. Res. Chem.* 112:320–326 (Apr. 15, 1983) have reported on the synthesis of the carboxy-terminal fourteen amino acid residues of a material they refer to as $ST_h$. That synthetic molecule was reported to have biologic activity 2–5 times that of the native $ST_h$ on a molar basis, using a suckling mouse assay.

In an oral presentation on Aug. 29, 1982 by Duflot et al., *Proceedinqs European Peptide Symposium:*683–686, published in Berlin in June of 1983, those workers reported the synthesis of porcine and human ST 18-mer polypeptides having their Cys mercapto groups blocked (S-blocked) with acetamidomethyl groups. Those amino acid residue sequences were purportedly identical to the sequences reported by So et al, supra, for ST Ia and by Chan et al., supra, for ST Ibh. However, the seventh amino acid residue from the amino-terminus of the sequences reported by Duflot et al. was a glycine residue (Gly), while that residue in the beforedescribed sequences is a glutamic acid residue (Glu).

Duflot et al. reported that immunization of mice or rabbits with their S-blocked porcine ST toxin coupled to tetanus toxoid or ovalbumin produced antibodies that recognized the natural or the synthetic toxins equally. Substantially no biologic activity in the suckling mouse assay was reported for the S-blocked, porcine, synthetic polypeptide toxin. Those authors reported the lack of biologic activity to be due to the absence of intramolecular disulfide bonds in the S-blocked molecule, which is in keeping with the prior report of Staples et al., supra.

The ST polypeptides contemplated herein include at least the carboxy-terminal 14-residue of ST Ibh and ST Ibp (ST Ia). That polypeptide may also include up to four, preferably three or fewer, and most preferably two or fewer, alternative amino acid residues to the six Cys residues of the ST sequence. In addition, where Cys residues are present, up to four, preferably three or fewer, and most preferably two or fewer, sulfur atoms of the Cys residues present may be alkylated.

A useful ST polypeptide contains at least one intramolecular cystine disulfide bond. Consequently, the presence of one or more alternative amino acid residues to a Cys residue, and of one or more alkylated Cys mercaptan groups is subject to a proviso that the ST polypeptide be capable of forming at least one intramolecular cystine disulfide bond. This proviso is discussed in detail hereinafter.

A useful 14-residue ST polypeptide sequence that corresponds to the carboxy-terminal 14 residues of ST, written from right to left and in the direction from amino-terminus to carboxy-terminus, corresponds to Formula II, below.

Formula II $R_a^1$ $R_b^2$ $R_c^3$ $R_d^4$

Cys($R_g^7$)Cys($R_h^8$)GluLeuCys($R_i^9$)Cys($R_j^{10}$)

Tyr(Asn)ProAlaCys($R_k^{11}$)AlaGlyCys($R_l^{12}$)Asn(Tyr)

$R_e^5$ $R_f^6$ wherein the two, specific amino acid residues in parentheses (Asn and Tyr) are each an alternative to the immediately preceding amino acid residue in the sequence of the formula;

a, b, c, d, e and f (a-f) and g, h, i, j, k and l (g-l ) are integers each having a value of zero or one, with the proviso that if the value of any of a-f or g-l is zero, the corresponding $R_a^1$, $R_b^2$, $R_c^3$, $R_d^4$, $R_e^5$ or $R_f^6$ ($R_{a\text{-}f}^{1\text{-}6}$-) group or $R_g^7$, $R_h^8$, $R_i^9$, $R_j^{10}$, $R_k^{11}$ or $R_l^{12}$ ($R_{g\text{-}l}^{7\text{-}12}$-) group is absent, and when an $R_{a\text{-}f}^{1\text{-}6}$-group is absent the sulfur atom of the Cys residue having an absent $R_{a\text{-}f}^{1\text{-}6}$-group forms a cystine disulfide bond, while if value of any one of a-f or g-l is one, the corresponding $R_{a\text{-}f}^{1\text{-}6}$- or $R_{g\text{-}l}^{7\text{-}12}$-group is present;

the $R_{a\text{-}f}^{1\text{-}6}$-groups when taken individually, are the same or different moieties bonded to the sulfur atom of the Cys residue and are selected from the group consisting of hydrogen, an alkyl group containing 1 to about 4 carbon atoms such as methyl, ethyl, iso-propyl, and sec-butyl, and a substituted alkyl group containing 2 to about 4 carbon atoms such as carboxymethyl, carbamoylmethyl, carboxyethyl and carbamoylethyl;

$R_{g\text{-}l}^{7\text{-}12}$ are the same or different alternative amino acid re to each immediately preceding Cys residue shown in the formula, and are selected from the group of amino acid residues having neutral a side chain, such as alanine (Ala) and serine (Ser); and at least two of a-f and two of g-l are zero and two non-contiguous Cys residues are present with the proviso that the synthetic ST polypeptide portion of the composite LT/ST polypeptide have the capacity of forming at least one intramolecular cystine disulfide bond formed from the at least two Cys residues present.

When in monomeric form, the above at least one disulfide bond is an intramolecular, intrapolypeptide cystine disulfide formed between the at least two Cys residues present in the ST polypeptide. When the ST polypeptide is in a polymeric form that contains a plurality of LT polypeptide-containing repeating units, the above at least one disulfide bond may be an intramolecular, intrapolypeptide cystine disulfide formed between the at least two Cys residues present in each ST polypeptide repeating unit. That at least one disulfide bond may also be an intramolecular, interpolypeptide cystine disulfide bond formed between one of the at least two Cys residues present in a first ST-containing repeating unit and another one of the at least two Cys residues present in a second ST-containing repeating unit or one of the Cys residues that may be present in another polypeptide repeating unit. It is therefore seen that an intramolecular cystine disulfide bond is present in both monomeric and polymeric composite forms of ST. In the monomeric ST-containing composite, that cystine disulfide bond is an intrapolypeptide bond, while in a polymer that includes an ST polypeptide sequence in the repeating unit, the disulfide may be an interpolypeptide or an intrapolypeptide bond.

In more preferred practice for the monomeric and polymeric forms of a composite LT/ST polypeptide containing a synthetic ST polypeptide portion, with reference to the above ST synthetic polypeptide of Formula II:

"e" is zero when "a" is zero,
"d" is zero when "b" is zero, and
"f" is zero when "c" is zero; and
each of "g" and "k" is zero when "a" is zero,
each of "h" and "j" is zero when "b" is zero, and
each of "i" and "l" is zero when "c" is zero.

The sequence shown in Formula II without the two specific alternative amino acids and subsituent and alternative R-groups corresponds to the carboxy-terminal fourteen amino acid residue sequence of ST Ibh. The fourteen amino acid residues comprising amino acids 59–72 of ST Ia (the carboxy-terminal fourteen residues of ST Ibp) differ from the sequence illustrated in Formula II without its alternative amino acids and R-groups at position 65 wherein an asparagine (Asn) residue replaces the tyrosine (Tyr) residue at the position numbered 11 from the amino-terminus of ST Ibh (residue position 8 from the carboxy-terminus), and at position 18 from the amino-terminus of ST Ibp (carboxy-terminus) wherein a tyrosine residue replaces the asparagine residue shown.

Thus, the Tyr residue to the immediate right of the forth Cys residue from the amino-terminus (Tyr-65 of ST Ia) may be replaced by the Asn residue that is parenthesized in Formula II, above. Conversely, the carboxy-terminal Asn shown may be replaced by a Tyr, as is shown by the parenthesization of the final Tyr residue.

It is particularly preferred that at least one of the four amino-terminal amino acid residues present in the sequence of the eighteen residue ST Ibh and ST Ibp molecules also be present in its natural positional sequence in the synthetic ST portion of a composite LT/ST polypeptide, or in any other entity that contains an ST polypeptide. It is still more preferred that all four of those additional amino acids be present in the synthetic ST portion in the same, natural positional sequence that they are present in ST Ibh and ST Ibp.

The preferred four additional amino acids at amino-terminus of an ST polypeptide correspond to amino acid position numbers 55 through 58 of ST Ia (positions 1 through 4 of ST Ibp) and are identical to those four amino-terminal amino acids in ST Ibh. The 4 amino acid polypeptide (4-mer) additionally present at the amino-terminus of the synthetic ST of Formula II in a preferred embodiment has a sequence, taken from left to right and in the direction from amino-terminus to carboxy-terminus, represented, as shown below in Formula III:

Formula III

AsnThrPheTyr

Thus, a preferred ST polypeptide has a sequence of 18 residues that is identical to the sequences of ST Ibh or ST Ibp (ST Ia) shown before. A useful ST polypeptide may also include an Asn residue at the carboxy-terminus and an Asn residue at the position numbered 11 from the amino-terminus of ST Ibh. Conversely, both residues may be Tyr residues. The four useful ST 18 residue sequences so defined are shown below in Formula IV, written as before described.

| FORMULA IV |
| --- |
| (A) AsnThrPheTyrCysCysGluLeuCysCysAsnPro |
| (B) AsnThrPheTyrCysCysGluLeuCysCysTyrPro |
| (C) AsnThrPheTyrCysCysGluLeuCysCysTyrPro |
| (D) AsnThrPheTyrCysCysGluLeuCysCysAsnPro |
| AlaCysAlaGlyCysTyr |
| AlaCysAlaGlyCysTyr |
| AlaCysAlaGlyCysAsn |
| AlaCysAlaGlyCysAsn |

The four sequences of Formula IV may be written as a single sequence using parenthesized, alternative residues. The combined ST polypeptide sequence, written as before-described, and using the amino acid residue sequence of ST Ibh as the basis of the alternative residues, is represented by the formula of Formula V, below.

FORMULA V

| FORMULA V |
| --- |
| AsnThrePheTyrCysCysGluLeuCysCysTyr(Asn)Pro |
| AlaCysAlaGlyCysAsn(Tyr) |

wherein the specific, parenthesized amino acid residues are an alternative to each of the immediately preceding residues shown in the formula.

Unless otherwise so designated herein, references to ST or an ST polypeptide refer to an ST-related polypeptide amino acid residue sequence that includes the alternative amino acid residues. This is true for 14 residue polypeptides, 18 residue polypeptides and those containing 15–17 residues.

The preferred 18-residue ST sequence that includes $R_{a-f}^{1-6}$-and $R_{g-l}^{7-12}$-groups and alternative amino acid residues, written from left to right and in the direction from amino-terminus to carboxy-terminus, is represented by the formula of Formula VI, below.

FORMULA VI

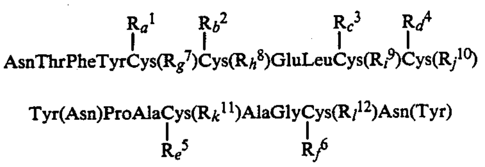

wherein $R_{a-f}^{1-6}$, $R_{g-l}^{7-12}$, and the specific, parenthesized amino acid residues are as are before-described.

The monomeric, composite LT/ST polypeptide contains at least one intramolecular, intrapolypeptide disulfide bond, more preferably two intramolecular, intrapolypeptide disulfide bonds and most preferably three intramolecular, intrapolypeptide disulfide bonds. The disulfide bonds are believed to be formed between the pairs of Cys residues of $R_a^1$ and $R_e^5$, and $R_b^2$ and $R_d^4$ as well as between the Cys residues of $R_c^3$ and $R_f^6$, when a-f have the value of zero.

However, the Cys residues of $R_a^1$ and $R_b^2$ as well as those of $R_c^3$ and $R_d^4$ are adjacent, contiguous pairs. Consequently, composite LT/ST polypeptides containing one disulfide bond can have substantially similar secondary structures and antigenicities regardless of whether that single disulfide bond is formed between the Cys residues of $R_a^1$ and $R_e^5$ or of $R_b^2$ and $R_e^5$. Similar results pertain to secondary structures formed due to disulfide formation between the Cys residues of $R_a^1$ and $R_d^4$ rather than $R_b^2$ and $R_f^6$, and the like.

A composite LT/ST polypeptide that is synthesized prior to the oxidative formation of an intramolecular, intrapolypeptide disulfide bond contains at least two Cys residues, so the value of at least two of g–l are zero and the corresponding $R_{g-l}^{7-12}$ groups are absent. In view of the similarity of secondary structure that is provided by formation of an intramolecular, intrapolypeptide cystine disulfide bond between one of two contiguous Cys residues and another Cys residue, a proviso is added that at least one pair of non-contiguous Cys residues from the Cys residues preceding the $R_{g-l}^{7-12}$-groups is present. That pair is selected from the group consisting of Cys residues that precede $R_g^7$,$R_h^8$ and $R_i^9$,$R_j^{10}$; $R_g^7$,$R_h^8$ and $R_k^{11}$; and $R_i^9$,$R_j^{10}$ and $R_l^{12}$. In terms of the amino acid residue positions in ST-portions of ST-containing entities, the pairs of non-contiguous Cys residues in synthetic ST portions are selected from the group consisting of those numbered 5 or 6 and 9 or 10, 5 or 6 and 14, and 9 or 10 and 17 from the amino-terminus of an ST 18 residue polypeptide portion.

The composite LT/ST polypeptides and network polymers containing the composite LT/ST polypeptides as repeating units are antigens to sera (antibodies) induced by both the LT B-subunit (as well as by the whole LT toxin) and biologic, native ST. Such antigenicities are discussed in detail in the RESULTS Section VI, hereinafter.

Broadly, however, the percentage of antigenicity of a composite LT/ST polypeptide containing a synthetic ST sequence as well as an LTB sequence is a relative measure of the amount of anti-biologic ST antibody that recognizes (binds to) a synthetic ST compared to biologic ST recognized by the same anti-biologic ST antibodies, and the similarly measured anti-LTB antibody that recognizes (binds to) a synthetic LTB polypeptide portion compared to LTB recognized by the same anti-LTB antibodies. Antigenicity calculations are based upon the weight of antigens used, and are independent of whether the antigen assayed is in monomeric or polymeric form.

Preferred LTB polypeptides, composite LT/ST polypeptides and network polymers containing LTB polypeptide repeating units such as composite LT/ST polypeptide repeating units exhibit at least about 5 percent of the antigenicity of the native LT B-subunit. Composite LT/ST polypeptides and network polymers containing composite LT/ST polypeptide repeating units also preferably exhibit at least about 10 percent of the antigenicity of native ST.

Suitable antigenicity and immunogenicity has also been found for synthetic ST-containing molecules wherein the sulfur atoms of Cys residues comprise portions of linkages other than cystine disulfide linkages. Because of that fact, the Cys residues of the above sequence of Formulas II and VI for synthetic ST portions of composite polypeptides are shown as bonded to $R_{a-f}^{1-6}$-groups whose identities are discussed hereinbelow.

It is noted however, that because at least one intramolecular, intrapolypeptide cystine disulfide bond is required for antigenic activity in the monomeric synthetic ST, and biological activity when that is desired, all six of the $R_{a-f}^{1-6}$-groups other than hydrogen may not be present in one synthetic ST polypeptide. Rather, at most, only four of those groups may be present in any one molecule. Thus, for example, where the Cys residues of $R_a^1$ and $R_e^5$ are combined to form an intramolecular, intrapolypeptide cystine disulfide bond, the values of "a" and "e" are zero, the $R_a^1$- and $R_e^5$-groups are absent and only $R_b^2$, $R_c^3$, $R_d^4$, and $R_f^6$ may be present in a monomeric synthetic ST molecule. Where "a" and "e" are zero, "g" and "k" are zero and $R_g^7$ and $R_k^{10}$ are absent.

To account for the presence of one, two or three intramolecular disulfide bonds of cystine residues formed among the six Cys residues, each of the R-groups 1–6 has also been labeled with a subscript letter a–f. Each subscript letter represents an integer having a value of zero or one. For more preferred embodiments, the proviso is added that "e" is zero when "a" is zero, "d" is zero when "b" is zero, and "f" is zero when "c" is zero, with the further proviso that at least one of "a", "b" or "c" must be zero, with the still further proviso that a disulfide bond is present between the respective pairs of Cys residues for which one subscript value of zero requires another subscript value to also be zero.

Each of the $R_{a-f}^{1-6}$-groups present in the synthetic ST may be hydrogen. In such a case, the Cys residue to which $R_{a-f}^{1-6}$-group is bonded is unsubstituted inasmuch as hydrogen is a normal group bonded to the sulfur atom of a Cys residue. The presence of hydrogen bonded to the sulfur atom of a cysteine is denoted herein by the designations Cys or CysH.

The $R_{a-f}^{1-6}$-groups may also be alkyl groups that contain 1 to about 4 carbon atoms. Exemplary of such $R_{a-f}^{1-6}$-groups are methyl, ethyl, propyl, i-propyl, n-butyl, sec-butyl, and the like.

The $R_{a-f}^{1-6}$-groups may further be substituted alkyl groups containing 2 to about 4 carbon atoms wherein the substituents include, hydroxy, carboxy, and carboxamido. Exemplary of such substituted alkyl groups are 2-hydroxyethyl, 2-hydroxypropyl, carboxymethyl ($-CH_2CO_2H$), carboxamidomethyl ($-CH_2CONH_2$), carboxyethyl ($-CH_2CH_2CO_2H$) and carboxamidoethyl ($-CH_2CH_2CONH_2$).

The $R_{a-f}^{1-6}$-groups may be present separately in a composite LT/ST polypeptide molecule, or mixtures of $R_{a-f}^{1-6}$-groups may be present in one polypeptide or polypeptide repeating unit. When all of the subscript letters a–f of a monomeric ST polypeptide-containing entity have a value of zero, the $R_{a-f}^{1-6}$-groups are absent, and three intramolecular, intrapolypeptide cystine disulfide bonds are present in an oxidized polypeptide.

The subscript letters a–f may also all have values of zero and the $R_{a-f}^{1-6}$-groups be absent in a network polymer containing ST polypeptide repeating units wherein intramolecular, interpolypeptide cystine disulfide bonds between and/or among synthetic ST polypeptide-containing portions of repeating units are present. Intramolecular, intrapolypeptide cystine disulfide bonds within the synthetic ST-containing portions of repeating unit portions may also be present in a network polymer.

On the average, the ST polypeptide repeating units in a network polymer contain at least about two such interpolypeptide cystine bonds per repeating unit. Consequently, in preferred practice at least four of a–f and four of g–l have a value of zero for such polypeptide repeating units, and at least four $R_{a-f}^{1-6}$-groups and four corresponding $R_{g-l}^{7-12}$-groups are absent due to the formation of the at least two interpolypeptide cystine disulfide bonds, and typically, one intrapolypeptide bond.

Antigenicity and immunogenicity can also be obtained using composite LT/ST polypeptides containing at least one intramolecular, intrapolypeptide cystine disulfide bond between the pairs of Cys residues such as those shown in Formulas II and VI as bonded to $R_a^1$ and $R_e^5$, $R_b^2$ and $R_d^4$, or $R_c^3$ and $R_f^6$, corresponding to the positions numbered 5 and 10, 6 and 14, and 9 and 17 from the amino-terminus of the ST Ibh or ST Ibp polypeptide portions, respectively, when the Cys residues not included in the disulfide bond are replaced by the same or different alternative amino acid residues, such as Ser residues.

The preferred alternative amino acid residues to the Cys residues of Formulas II and VI contain neutral side chains and thus provide no ionic charge to the synthetic polypeptide when the synthetic polypeptide is dissolved in an aqueous solution of physiological pH values; i.e., the preferred alternative amino acid residues are free from ionic charges when part of a composite LT/ST polypeptide, and are in aqueous solution. The amino acid residues alanine (Ala) and serine (Ser) are exemplarly of preferred alternative amino acids that are useful for replacing Cys residues.

The alternative amino acid residues to the non-disulfide-bonding Cys groups are illustrated in the above Formulas II and VI by the parenthesized groups $R_g^7$, $R_h^8$, $R_i^9$, $R_j^{10}$, $R_k^{11}$ and $R_l^{12}$ each of which can replace the preceding Cys residue (the adjacent Cys residue toward the amino-terminus), and wherein the subscripts g–l are integers having the value of zero or one. In preferred synthetic ST polypeptides, if "a" is zero, "g" and "k" are each zero; if "b" is zero, "h" and "j" are each zero; and if "c" is zero, "i" and "l" are each zero.

The above disclosure as to groups $R_a^1$-$R_f^6$ and $R_g^7$-$R_l^{12}$ is equally applicable to composite LT/ST polypeptides containing ST polypeptide portions including the carboxy-terminal fourteen amino acid residues shown in Formula II, and to the more preferred synthetic ST-containing composite LT/ST polypeptide containing eighteen amino acid residues whose sequence is shown in Formula VI. That disclosure is also applicable to composite LT/ST polypeptides whose amino acid residue sequences correspond to the carboxy-terminal 14 residues of ST and additionally include at their amino terminii one, two or three residues from the carboxy-terminus of the sequence illustrated in Formula III bonded to the amino-terminus of the 14-residue polypeptide in their naturally occurring sequences, as shown. Thus, the above disclosure is also applicable to a composite LT/ST polypeptide whose amino acid residue sequence corresponds to the 14 carboxy-terminal ST residues plus an additional Tyr, PheTyr, or ThrPheTyr peptide bonded to the amino-terminus of the 14 residue ST sequence.

A composite LT/ST polypeptide of this invention may have its LTB polypeptide portion bonded at the amino-terminal or carboxy-terminal ends of the ST polypeptide. The designation "composite LT/ST polypeptide" is meant to include both arrangements of the LT polypeptide portion relative to the LT polypeptide portion.

As already noted, the LT and ST polypeptide portions are bonded through a peptide bond. In particularly preferred embodiments, the two polypeptide portions of a composite LT/ST polypeptide are peptide-bonded directly to each other. Thus, the carboxy-terminal residue of one polypeptide portion is peptide-bonded to the amino-terminal residue of the other polypeptide portion. Indeed, a composite LT/ST polypeptide is preferably synthesized in a single polypeptide preparation. Composite polypeptides containing both amino-terminal and carboxy-terminal LTB polypeptides are illustrated hereinafter.

In other embodiments, the ST and LTB polypeptide portions are separated by one or two peptide-bonded additional amino acid residues that are typically added to improve the solubility of the composite polypeptide, a conjugate of which it may be a part, or a network polymer of which a composite LT/ST polypeptide is a repeating unit. The additional amino acid residues separating the LTB and ST polypeptide portions are not present in the LTB or ST sequence and are those that have side chains that provide an ionic charge to the composite LT/ST polypeptide at the pH value of the jejunum; i.e., about pH 6.5. Such amino acid residues thus contain acidic or basic side chains and are exemplified by Asp or Glu, and Lys or Arg, respectively.

When two additional amino acid residues separate the LTB and ST polypeptide portions of a composite LT/ST polypeptide, the two residues need not be the same, but those residues do provide the same ionic charge to the composite LT/ST polypeptide at pH 6.5. Thus, two Glu residues, two Asp residues or a Glu and an Asp residue may be used together. Similarly, two Lys residues, to Arg residues or an Arg and a Lys residue may be used together. However, a Glu and an Arg or an Asp and Lys, for example, are not used together.

The amino- and/or carboxy-terminii of a composite LT/ST polypeptide (a) as a conjugate when linked to a carrier, (b) free, or (c) most preferably as a repeating unit of a network polymer, may also include up to about four additional, ionic charge-providing (acidic or basic side chain-providing) amino acid residues as described before. Preferably, two such additional residues are utilized, and again, those residues preferably are those that contain basic side chains; i.e., Arg and Lys.

A composite LT/ST polypeptide of this invention may thus be described by Formula VII, below.

Formula VII $$(X)_n\text{-}(A)_o\text{-}(Z)_r\text{-}B\text{-}(Z)_s\text{-}(A)_p\text{-}(Y)_m$$

wherein

X, Y and Z, when present are amino acid residues that are
- (a) selected from the group consisting of Lys and Arg residues, or
- (b) selected from the group consisting of Asp and Glu residues;

"n" and "m" are integers having a value of zero, 1,2,3 or 4, such that the respective X and Y are absent when either or both of "n" and "m" have a value of zero, while the respective X and Y residues are present when either or both of "n" and "m" have a value of other than zero, with the average number of X and Y residues present per polypeptide being equal to the values of X and Y, respectively;

"r" and "s" are integers having a value of zero, 1 or 2, such that the respective Z is absent when either or both of "r" and "s" have a value of zero, while the respective Z is present when "r" and "s" are present, the average number of Z residues per composite LT/ST polypeptide molecule or repeating unit being equal to the value of "r" or "s", with the proviso that when either of "r" or "s" is greater than zero, the other of "r" or "s" is zero and the respective Z whose "r" or "s" is zero is absent;

"o" and "p" are integers having the value of zero or 1 so that the corresponding A is absent when either of "o" and "p" have a value of zero, with the proviso that "o" and "p" may not both have the same value;

A is a polypeptide containing about 10 to about 35 amino acid residues corresponding in sequence to the amino acid residue sequence of about position 35 to about position 95 from the amino-terminus of the B-subunit of the heat-labile enterotoxin of *Escherichia coli,* wherein the position numbers include the 21 residue signal polypeptide of said B-subunit; and B is a polypeptide containing up to 18 amino acid residues corresponding in sequence to at least the carboxy-terminal 14 residues of the heat-stable enterotoxin of *Escherichia coli.*

The polypeptide sequence denominated "A" in Formula VII may be any of the LTB polypeptides disclosed herein. However, as noted before, preferred LTB amino acid residue sequences include about 15 to about 30 residues corresponding in sequence to about position 55 to about position 85 from the amino-terminus of the LT B-subunit. Most preferred LTB sequences contain about 20 to about 25 amino acid residues that correspond in sequence to about position 60 to about position 85 from the amino-terminus of the LT B-subunit.

Exemplary LTB polypeptides are illustrated in the RESULTS Section (VI) that follows.

The polypeptide sequence denominated "B" in Formula VII may be any of the ST polypeptides disclosed herein. Preferably, as already noted, the ST polypeptide portion contains the 18 residue sequence of either ST Ibh or ST Ibp that may also be defined as the carboxy-terminal 18 residues of an ST polypeptide inasumch as the 72 residue sequence encoded by the ST Ia genome terminates with the same 18 residue sequence as that of ST Ibp. In addition, the preferred ST polypeptide portion contains at least four of a–f and four of g–l that are zero. Most preferably the ST polypeptide portion is free of $R_{a\text{-}f}^{1\text{-}6}$-groups bonded to Cys mercaptans (sulfur atoms), and in the ultimately used polypeptide or polypeptide repeating unit, substantially all of the Cys residues are present in oxidized form as cystine residues that form intramolecular, intrapolypeptide disulfide bonds in monomeric composite LT/ST polypeptides, or that form intramolecular, intrapolypeptide and interpolypeptide disulfide bonds in network polymers containing composite LT/ST polypeptides as repeating units. Thus, most preferably, all of a–f and g–l are zero.

Monomeric composite LT/ST polypeptides are typically prepared by air oxidation of a reduced composite LT/ST polypeptide-containing oxidation medium containing the polypeptide at a concentration of less than about 0.5 milligrams per milliliter (mg/ml). More preferably, the concentration is about 0.1 to about 0.25 mg/ml. Lower concentrations may be utilized, but typically produce too little of the monomeric, oxidized composite LT/ST polypeptide to be useful for most purposes. Diminishing amounts of monomeric polypeptide are produced at concentrations above about 0.25 mg/ml.

Oxygen present in the ambient air is preferably utilized as the oxidizing agent. Other oxidants such as hydrogen peroxide and the ferricyanide ion may be used, but are not preferred.

Oxidation is carried out with gentle, or no stirring until free mercaptan groups are no longer detected by the Ellman test. [Ellman, *Arch. Biochem. Biophys.* 82:70–77(1959).] This oxidation is typically carried out over a time period of 1 to about 24 hours, and is generally completed after about 8 hours where three intramolecular, intrapolypeptide cystine disulfide bonds are formed. Two or one intramolecular, intrapolypeptide bonds are typically formed in less than about 8 hours.

The reduced, composite LT/ST polypeptide is dissolved or dispersed in an oxidation medium having a pH value of about 7.5 to about 10.5. Air oxidations are preferably carried out at about a pH value of about 7.0 to about 9.5. More preferably, the oxidation is carried out at a pH value of about 7.5 to about 8.0. The oxidation is typically carried out at ambient, room temperatures, but is preferably carried out at a temperature of about 0° C. to about 25° C.

Upon completion of the oxidation reaction, the oxidized composite LT/ST polypeptide is typically collected as by lyophilization. The dried material so collected may be used as is or may be purified as by column chromatography using an ion exchange resin or a gel exclusion matrix as the stationary phase.

Previous studies have indicated that the intramolecular, intrapolypeptide cystine disulfide bonds in the monomeric synthetic ST are found to be formed between the first and fifth, second and fourth, and third and sixth Cys residues from the amino-terminus; those Cys residues correspond to the residues of ST Ibh numbered 6 and 10, 5 and 14, and 9 and 17, respectively, from the amino-terminus. Those Cys residues also correspond to the Cys residues bonded to $R_a^1$ and $R_e^5$, $R_b^2$ and $R_d^4$, and $R_c^3$ and $R_f^6$, respectively, whose positions from the carboxy-terminus in the 18-residue ST polypeptide are analogous to the carboxy-terminal positions in the 14-residue polypeptide shown in Formula II.

The rate of intramolecular, intrapolypeptide cystine disulfide bond formation for monomeric synthetic ST polypeptides was found to be in the order of the Cys residues of $R_b^2$ and $R_d^4$, followed by Cys residues of $R_c^3$ and $R_f^6$, and then followed by the Cys residues of $R_a^1$ and $R_e^5$. Using numbering from the amino-terminus of ST Ibh, the order of disulfide bond formation was between the Cys residues numbered 6 and 10, then 9 and 17, followed by 5 and 14.

The primary and secondary structure of the monomeric synthetic ST Ibh, was, from amino-terminus to carboxyl-terminus, therefore:

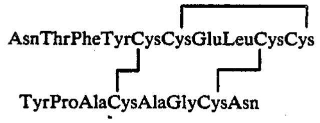

wherein the lines connecting the Cys residues represent the intramolecular, intrapolypeptide cystine disulfide bonds formed between those residues.

In view of the identity of ST-related amino acid residue sequences, the similarity of ST antigenicities exhibited by the ST-containing composite LT/ST polypeptides of this invention and the unsubstituted ST monomeric polypeptides previously prepared, it is believed that the secondary structures of the ST portions of monomeric composite LT/ST polypeptides are substantially similar to those of previously prepared ST polypeptides. Consequently, exemplary composite LT/ST polypeptides containing three intramolecular, intrapolypeptide cystine bonds are believed to have the primary and secondary structures represented by Formulas VIIIa and VIIIb, below.

Formula VIIIa

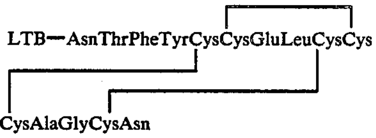

Formula VIIIb

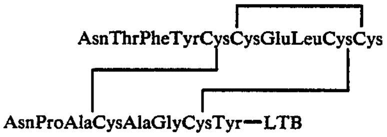

wherein "LTB-" is any of the previously described LTB polypeptides peptide-bonded to the amino-terminus of ST Ibh or to the carboxy-terminus of ST Ibp, respectively, and the lines connecting Cys residues represent the intramolecular, intrapolypeptide cystine disulfide bonds formed between those Cys residues.

Similarly, an exemplary composite LT/ST polypeptide containing two intramolecular, interpolypeptide cystine disulfide bonds, and free from $R_{g\text{-}l}^{7\text{-}12}$-groups is believed to have primary and secondary structures represented by the general Formula IX, below.

Formula IX

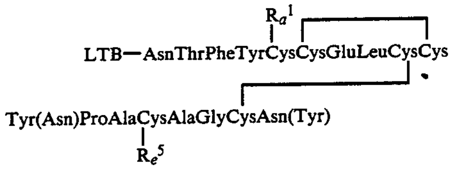

wherein LTB-, the lines connecting Cys residues, the parenthesized Asn and Tyr residues and $R_a^1$ and $R_e^5$ are as before described.

An illustrative composite LT/ST polypeptide containing a single intramolecular, intrapolypeptide cystine disulfide bond, and free of $R_{g-l}^{7-12}$-groups, is believed to have primary and secondary structures represented by Formula X, below.

FORMULA X

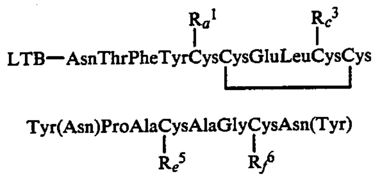

wherein the LTB-, the line connecting Cys residues, the parenthesized Asn and Tyr residues, and $R_a^1$, $R_c^3$, $R_e^5$ and $R_f^6$ are as before described.

It is to be remembered that the LTB polypeptide may be bonded at the carboxy-terminus of the ST sequence portion of a composite LT/ST polypeptide, that up to two additional residues providing charged side chains at pH 6.5 may be between the LTB and ST portions of the composite, and that one through four additional acid or base side chain-containing residues providing the same ionic charge at pH 6.5 may be bonded at the terminii of either or both of the LTB and ST portions of the composite.

III. POLYMERS CONTAINING LTB POLYPEPTIDE REPEATING UNITS

Polymers that contain a before described LTB polypeptide repeating unit are particularly preferred embodiments of this invention.

Polymers have several advantages over similar monomeric composite LT/ST polypeptides or the monomeric form of an LTB polypeptide. First, when used as an immunogen, the polymers do not require a carrier protein. Second, the polymers generally exhibit substantially none of the biologic activity of either of the naturally occurring LT B-subunit or ST toxins, when ST is an included polymeric repeating unit. Third, when both LTB and ST polypeptide repeating units are present in a polymer, the immunogenicities of both repeating units of the polymers are typically improved over similar monomeric materials of the same sequences, particularly for the ST portion of the polymers.

A. Linear Polymers

Linear polymers comprise one group of the LTB polypetpide repeating unit-containing polymers contempIted. Such materials contain a plurality of before-described LTB polypeptides as repeating units. In the reduced, monomeric form, each LTB polypeptide includes an additional Cys residue peptide-bonded to its amino-terminus and an additional Cys residue peptide-bonded to its carboxy-terminus. The polypeptide so constituted is referred to as a diCys-LT polypeptide.

Oxidation of a diCys-LT polypeptide, as described hereinafter, provides a linear polymer containing a plurality of LTB polypepide repeating units. The repeating units of such a polymer are bonded together by intramolecular, interpolypeptide cystine disulfide bonds formed by oxidation of the terminal Cys residues peptide-bonded to the LTB polypeptide repeating units.

When the polymerization medium contains only diCys-LT polypetpides, a homopolymer results. If another polypeptide containing only two mercaptan-containing Cys residues such as a before-described ST polypeptide containing four Ser residues as alternatives to four of the Cys residues is admixed in the polymerization medium, a copolymer results.

Preliminary studies have been conducted using a polymer prepared by oxidation of a diCys-LT polypeptide whose LTB polypeptide repeating units corresponded in amino acid residue sequence to poistions 58 through 83 of LTB (diCys-$LT_{58-83}$). The results of those studies indicated an immunoreactivity similar to that obtained with a composite LT/ST polypeptide of the same LTB sequence as is described hereinafter.

B. Network Polymers

Network polymers that contain a before-described LTB polypeptide and ST polypeptide repeating units are particularly contemplated embodiments of this invention. These polymers are referred to as "network polymers" because it is believed that the polymers are extensively cross-linked due to their preparation by oxidation of ST-containing polypeptides that preferably contain six Cys residues that can form both intramolecular intrapolypeptide cystine disulfide and interpolypeptide cystine disulfide bonds, and thus form a cross-linked, three-dimensional network.

(1) Composite LT/ST Polypeptide Repeating Units

One network polymer of this invention contains a plurality of the before-described composite LT/ST polypeptides as repeating units. The repeating units are bonded together by intramolecular, interpolypeptide cystine disulfide bonds provided by oxidized cysteine (Cys) residues.

A network polymer is prepared from a reduced (cysteine-containing) form of a before-described composite LT/ST polypeptide that is oxidized by molecular oxygen in ambient air. A composite LT/ST polypeptide is oxidized at a concentration of greater than about 0.5 mg/ml, and more preferably at a concentration of about 1 to about 5 mg/ml, or higher up to the limit of composite LT/ST polypeptide solubility in the oxidation medium.

Again, oxidation is carried out with gentle or no stirring, and contact between the solution (oxidation medium) and oxidizing air is maintained for a time period of about one hour to about 24 hours, more preferably for about 8 hours, or until there is an absence of free mercapton groups as measured by the before-described Ellman test. Except for the concentration of the reduced form of a composite LT/ST polypeptide, oxidation to form a monomeric composite LT/ST polypeptide or a network polymer having a plurality of oxidized composite LT/ST polypeptides as repeating units is substantially identical.

Molecular weights of the network polymers of this invention may vary widely. Average molecular weights, range from about 20,000 daltons (20kd) to over one million daltons.

(2) LTB Polypeptide and ST Polypeptide Repeating Units

Another embodiment of a network polymer of this invention contains a plurality of first diCys-LT repeating units, as described before as well as a plurality of second, ST polypeptide repeating units, as described before wherein the ST polypeptide includes at least the 14 carboxy-terminal residues of ST as are illustrated in Formula II, and more preferably the 18 residues shown in Formula VI, and is free from a peptide-bonded LTB polypeptide. The polymer is thus a copolymer whose first-named and second polypeptide repeating units are bonded together by cystine disulfide bonds formed by oxidation of the Cys residues present in each of the repeating units.

The two repeating units may be present in the polymer in a mole ratio of about 10:1 to about 1:10. Preferably, the repeating units are present at a mole ratio of about 5:1 to about 1:5. Most preferably, the mole ratio of diCys-LT to ST repeating units is about 1:1 to about 3:1, since a preferred LTB polypeptide such as that corresponding to position 58 through 83 of the $LT_p$ B-subunit has been found to be about one-half to one-third as immunogenic as the native LT B-subunit while the ST polymers are typically equally or more immunogeinc than the native ST.

It is preferred that the ST polypeptide repeating units be free of $R_{a}$-$f^{1-6}$-groups bonded to Cys mercaptans and that substantially all of the Cys groups be present, as is discussed herein for the preparation of other polymers containing an ST polypeptide repeating unit, such as for composite LT/ST polypeptide repeating units because it is desirable to have at least one intramolecular, intrapolypeptide cystine disulfide bond, and two Cys residues are required for linear polymerization. Thus, two Cys residues are available for forming the cross-links of the network polymer.

These network copolymers are prepared from the reduced forms of the repeating units following the steps discussed hereinafter in Section IV for polymer preparation.

(3) Additional LTB Polypeptide-Containing Network Polymers

A still further group of LTB polypeptide-containing polymers are those copolymers that include repeating units comprised of (i) a diCys-LT polypeptide and (ii) a composite LT/ST polypeptide. These polymers may be prepared, following the oxidation procedures described hereinafter, by contacting molecular oxygen present in ambient air with an oxidation medium (solution or dispersion) that contains the reduced forms of a diCys-LT polypeptide and a composite LT/ST polypeptide. The repeating units of such a copolymer are also bonded together through cystine disulfide bonds of the oxidized Cys resiudes present in the reduced polypeptides.

These copolymers may contain the LTB polypeptide repeating unit provided by a diCys-LT polypeptide and the LT/ST repeating unit provided by a composite LT/ST polypeptide in a mole ratio of about 0.25:1 to about 5:1. More preferably, the mole ratios utilized are about 1:1 to about 2:1, in the order recited. The mole ratio of total LTB polypeptide-containing repeating units to ST polypeptide repeating units in such a polymer is thus about 1.25:1 to about 6:1, and more preferably about 2:1 to about 3:1.

It is noted that the LTB polypeptide sequence in both LTB polypeptide-containing repeating units need not be the samea. Preferably, however, both are the same and correspond to a previously described particularly preferred LTB polypeptide sequence.

IV. GENERAL SYNTHETIC PROCEDURE FOR OXIDIZING ST-CONTAINING POLYPEPTIDES AND FOR PREPARING POLYMERS

A general synthetic procedure for preparing a monomeric material that includes an ST polypeptide such as a composite LT/ST polypeptide and for preparing polymers that contain LTB polypeptide repeating units based upon the results discussed hereinafter and several other determinations is as follows:

(1) A monomeric, first polypeptide containing Cys residues in the reduced form is prepared in the substantial absence of oxidizing agent. The first polypeptide includes the amino acid residue sequence of an LTB polypeptide of this invention such as a diCys-LT polypeptide or a composite LT/ST polypeptide, with or without the before-discussed additional amino acid residues, and is substantially free from intramolecular, cystine disulfide bonds.

(2) The first polypeptide so prepared is provided, and is dissolved or dispersed in an aqueous oxidation medium at a concentration of about 5 mg/ml, more preferably at a concentration of less than about 2 mg/ml, and most preferably at a concentration of about 1 mg/ml to about 0.5 mg/ml for preparing a polymer; and at less than about 0.5 mg/ml, and more preferably at about 0.25 to about 0.1 mg/ml for preparing a monomeric composite LT/ST polypeptide. The pH value of the oxidation medium into which the first polypeptide is dissolved or dispersed is preferably alkaline and less than about 10.5, and more preferably is about 7.5 to about 10.5.

(3) The first polypeptide-containing oxidation medium is thereafter contacted with molecular oxygen in the air as an oxidizing agent. The pH value of the medium during oxidation is preferably about 7.0 to about 9.5, more preferably about 7.5 to about 9, and most preferably about 7.5 to about 8.0. The medium is preferably contacted with ambient air, with or without gentle stirring.

(4) Contact between the oxidation medium and the air is maintained for a period of about 1 to about 24 hours, and more preferably for about 2 to about 8 hours, to form at least one intramolecular, intrapolypeptide or interpolypeptide cystine disulfide bond from the Cys (CysH) residues present. For monomeric composite LT/ST polypeptides, the at least one cystine disulfide bond is an intramolecular, intrapolypeptide bond, while for a polymer the at least one cystine disulfide is an intramolecular, interpolypeptide bond. It is preferred that each ST polypeptide-containing repeating unit of a polymer form an average of about two interpolypeptide cystine disulfide bonds so that polymers having more than two composite LT/ST polypeptide repeating units are formed.

In preferred practice for monomeric composite LT/ST polypeptides, the disulfide bond is formed between the Cys residues preceding the pairs $R_g^7$ and $R_k^{11}$, $R_h^8$ and $R_j^{10}$, and $R_i^9$ and $R_l^{12}$ of Formulas II and VI, which correspond to the positions of the residues numbered 5 and 14, 6 and 10, and 9 and 17 from the amino-terminus of the ST Ibh or ST Ibp molecule, respectively. In more preferred practice, contact between molecular oxygen and the solution is maintained for a time period sufficient to form two disulfide bonds, preferably between the above-mentioned pairs of Cys residues, and still more preferably for a time period sufficient to form three disulfide bonds, again preferably between the above pairs of Cys residues.

The oxidation is preferably carried out at a temperature of about 0° C. to about 25° C.

(5) Upon completion of the oxidation reaction, the synthetic monomeric composite LT/ST polypeptide or polymer is typically collected as by lyophilization, and purified as by column chromatography.

V. IMMUNIZATIONS AND ANTIBODIES

A polypeptide conjugate, composite LT/ST polypeptide conjugate or polymer of this invention, when introduced into a mammalian host as a unit dose inoculum having an effective amount of polypeptide conjugate, composite LT/ST polypeptide conjugate or polymer in a physiologically tolerable diluent, is capable of inducing production of antibodies in the host mammal that immunoreact with the LT B-subunit alone, or with the LT B-subunit as well as an ST polypeptide, and preferably protect the host animal from in vivo infection caused by *E. coli* that secrete those toxins.

The "effective amount" of polypeptide conjugate, composite LT/ST polypeptide conjugate or polymer in a unit dose depends upon a number of factors. Included among those factors are the body weight of the animal immunized and the number of inoculations desired to be used. Individual unit dose inoculations typically contain about 10 micrograms to about 5 milligrams of polypeptide, composite LT/ST polypeptide or network polymer per kilogram body weight of the mammalian host. Usually used unit dosages typically contain about 0.5 milligrams per kilogram of host body weight. Inoculation methods and amounts in rabbits and rats, for the purposes of raising antibodies and protection when challenged by viable ETEC, respectively, are described hereinafter.

Polypeptides that are not repeating units of a polymer are administered as a conjugate of a polypeptide hapten covalently bound to a carrier. Useful carriers utilized herein include porcine immunoglobulin G (PIG), tetanus toxoid (TT) and keyhole limpet hemocyanin (KLH). Additional useful carriers include bovine serum albumin (BSA), human serum albumin (HSA), peanut agglutinin, olvalbumin, curcubin, poly L-(Lys:Glu), and the like.

Physiologically tolerable diluents are well known in the art. Exemplary of such diluents are distilled or deionized water, normal saline solutions and phosphate-buffered saline (PBS) solutions.

The immunizing composition or inoculum may be introduced into the host orally or by intravenous, subcutaneous or intraperitoneal injection, or the like, using known methods. Adjuvants such as complete Freund's adjuvant (CFA), incomplete Freunds's adjuvant (IFA), alum, tetanus toxoid and the like as are well known in the immunological arts may also be included in the inocula as part of the physiologically tolerable diluent. Booster injections may also be given, as desired, to build a desired antibody titer in the host's serum.

Exact dosages depend on the animal and polypeptide conjugate, composite LT/ST polypeptide conjugate or polymer used, and can be determined using known challenge techniques.

The term "inoculum" is used herein to mean any immunizing composition. As such, the term also embraces vaccines that are useful in man and other mammals for conferring in vivo protection against enterotoxin-producing *E. coli* strains. A given vaccine and inoculum may be identical where non-human mammalian hosts are involved, but typically differ where humans are the intended hosts. The reason for that difference is that adjuvants such as CFA are not utilized in humans, and another adjuvant must be used if any adjuvant is to be present in a human vaccine.

The term "unit dose" refers to physically discrete units suitable as unitary dosages for animals, each unit containing a predetermined quantity of active material calculated to produce the desired therapeutic effect in association with the required diluent or vehicle. The specifications for a novel unit dose of this invention are dictated by and are directly dependent on (a) the unique characteristics of the immunogen and the particular therapeutic effect to be achieved, and (b) the limitations inherent in the art of compounding such active materials for therapeutic use in animals.

Antibodies to a polypeptide, composite LT/ST polypeptide or polymer of the present invention can be used in assays or to treat ETEC infections. The antibodies can be used directly as whole, intact antibodies or may be processed to provide Fab or $F(ab')_2$ portions, all of which are biologically active. The term "antibody" indicates a whole, intact antibody or the idiotype-containing polyamide portion of the antibody that is biologically active and is capable of immunoreacting with or binding to its antigenic ligand; i.e., an intact LT toxin, its B-submit and/or native ST, as appropriate.

To manufacture antibodies, an immunizing inoculum described before is introduced into the host mammal as by injection. The host is maintained for a time sufficient for antibodies to be induced, usually for one to about four months. The desired antibodies induced are thereafter harvested from host fluids. The whole antibodies so induced can be used directly, or they may be cleaved with pepsin or papain as is well known to provide $F(ab')_2$ or Fab portions that may be used. The antibodies produced may also be used as therapeutic agents for passive immunoprophylaxis.

VI. RESULTS

A. Antigenicity of LTB Polypeptides

A series of polypeptides were synthesized that contained various lengths of amino acids from different regions of the 124 amino acid sequence of the LTB-subunit. Three exemplary polypeptides that had more than about 5 percent of the antigenicity of native B-subunit as determined by B/B ELISA (described in the MATERIALS AND METHODS Section), are shown schematically in FIG. 1. Values determined by $GM_1$/B ELISA (also described in the MATERIALS AND METHODS Section) were very similar to those obtained by B/B ELISA in each instance.

Two LTB polypeptides were synthesized sequentially together from the amino-terminus of the 18 amino acid residue sequence of ST Ibh to form composite LT/ST polypeptides. Oxidation of the composite LT/ST polypeptide to yield a network polymer having composite LT/ST polypeptides as repeating units, enhanced the antigenicity of the B-subunit polypeptide portion in that the B-subunit anitgenicity of the sequence corresponding to position 35 through position 55 of LTB rose to about 49 percent, and that of the sequence corresponding to position 58 through position 83 rose to about 95 percent that of native B-subunit (FIG. 1). The sequence of the two composite LT/ST polypeptides are shown hereinbelow, from left to right and in the direction of amino-terminus to carboxy-terminus, represented by the formulas of Formula XIa and Formula XIb, respectively:

Formula XIa

AsnThrGlnIleTyrThrIleAsnAspLysIle
LeuSerTyrThrGluSerMetAlaGlyLysAsnThrPhe
TyrCysCysGluLeuCysCysTyrProAlaCysAla-
GlyCysAsn

Formula XIb

MetValIleIleThrPheMetSerGlyGlu
ThrPheGlnValGluValProGlySerGlnHisIleAsp
SerGlnLysAsnThrPheTyrCysCysGluLeuCys-
CysTyr ProAlaCysAlaGlyCysAsn

The composite LT/ST polypeptide of Formula XIb was selected for further evaluation alone, linked to a carrier as a conjugate and as a repeating unit of a network polymer.

B. Immunogenicity of Monomeric Composite LT/ST Polypeptides

The immunogencity of the composite LT/ST polypeptide of Formula XIb was initially evaluated in its monomeric form by immunizing rats with this material given either alone or conjugated to a large molecular weight carrier, porcine immunolglobulin G (PIG). The polypeptide was conjugated to PIG using glutaraldehyde as coupling agent, using a polypeptide to PIG ratio of 2.35 to 1 by weight. The resulting conjugate contained 58 percent composite LT/ST polypeptide by weight. The antigenicity of the composite LT/ST polypeptide was not affected by the conjugation reaction, so 1 milligram (mg) of conjugate contained 580 B-subunit antigen units (AU).

Figure 3:
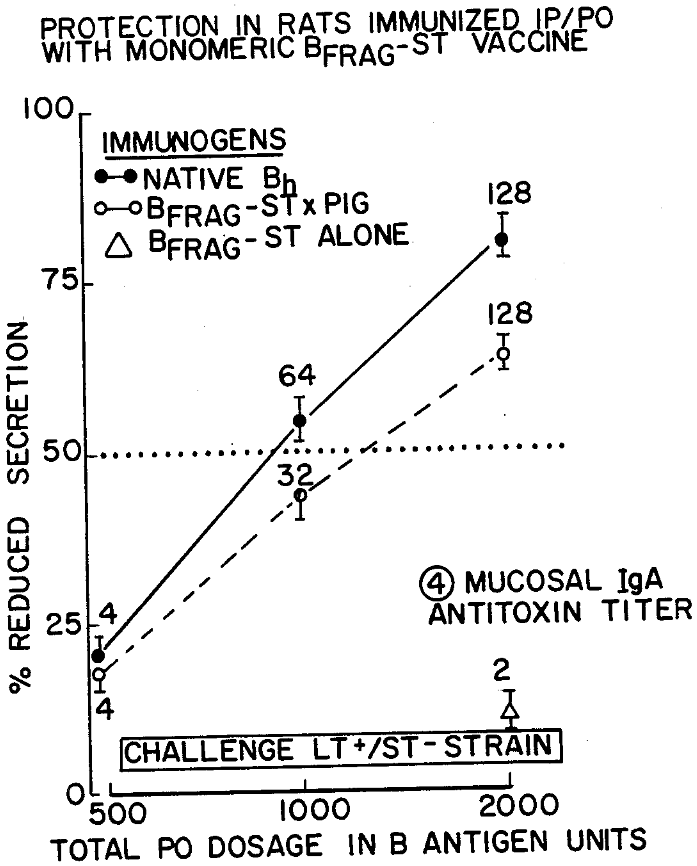
FIG. 3 is a graph illustrating the results of immunization of rats by primary parenteral immunization (IP) followed by two per oral (PO) immunizations. The ordinate shows the percentage of reduced intestinal secretion, while the abscissa reflects the total per oral dosage in $LT_h$ B-subunit (B) antigen units. Graded antigen unit dosages were introduced using vaccines containing as active ingredient (immunogen) either native $LT_h$ B-subunit (●—●; NATIVE $B_h$), or the monomeric form of an $LT_p$ B-subunit-related polypeptide peptide bonded to an 18-residue ST Ibh polypeptide (composite LT/ST polypeptide) alone (Δ; $B_{FRAG}$-ST ALONE) or conjugated to porcine immunoglobulin G (PIG) (○—○; $B_{FRAG}$-ST×PIG). Rats were challenged with viable LT+/ST− *E. coli* strain PB 258. Results are expressed as the mean ±SEM reduced secretion in immunized rats as compared with similarly challenged controls. Numerals above or below the data points indicate the mucosal IgA antitoxin titers for those FIG. 4 are graphs illustrating the results of immunization of rats by primary parenteral immunization (IP) followed by two per oral (PO) immunizations. Graded antigen unit dosages were introduced using vaccines containing as active ingredient (immunogen) a synthetic 18 residue ST Ibh polypeptide chemically cross-linked to the native $LT_h$ B-subunit [●—●; ST(S)XB] and a network polymer having the composite LT/ST polypeptide of FIG. 3 as repeating units [○--○; BFRAG-ST] in the left-hand panel, and the same network polymer [○--○; $B_{FRAG}$-ST] and native $LT_h$ B-subunit NATIVE $B_h$] in the right-hand panel. Challenges were done with viable *E. coli* $LT^+/ST^-$ strain Tx 452 in the left-hand panel, and with viable *E. coli* $LT^+/ST^-$ strain PB 258 in the right-hand panel. The ordinates for both panels are as described in FIG. 3. The abscissas show the total PO dosage in ST(S) and native $LT_h$ B-subunit antigen units for the left-and right-hand panels, respectively. The number of milligrams (mg) of immunogne corresponding to the antigen units of the abscissa are also shown. Other results are shown as in FIG. 3.

Rats were given intraperitoneal (IP) primary immunization with 200 AU of either native B-subunit or the composite LT/ST polypeptide followed by two per oral (PO) boosts of graded AU dosages. As is shown in FIG. 3, the conjugated polypetide raised the same titers of intestinal IgA antitoxin to B-subunit and provided only a slightly lesser degree of protection against challenge with the viable $LT^+/ST^-$ strain as that achieved by native B-subunit.

As anticipated, immunization with the low molecular weight unconjugated composite LT/ST polypeptide failed to raise an antitoxin response or to provide protection. These promising results with the conjugate led to making and characterizing the properties of the composite LT/ST polypeptide in polymerized form.

C. Properties of a Network Polymer Containing Composite LT/ST Polypeptide Repeating Units (1) Antigenicity. The antigenicity of another network polymer having repeating units corresponding to the sequence of the composite LT/ST polypeptide Formula XIb was 57 percent that of native B-subunit as determined by $GM_1$/B ELISA and 54 percent as determined by B/B ELISA; its ST antigenicity was 47 percent that of synthetic ST as determined by ST/ST ELISA (described in the MATERIALS AND METHODS Section).

(2) Toxicity. The network polymer exhibited a negative response in the Chinese hamster ovary (CHO) assay [Guerrant, *Infect. Immun.* 10:320–327, (1974)] at the maximum tested dosage of 100 micrograms (ug), which is 5 million times more than the minimum dosage of LT [20 nanograms (ng)] necessary to elicit a positive response in this assay. The network polymer exhibited a negative response in the suckling mouse assay [Giannella, *Infect. Immun.* 14:95–99, (1976)] at the maximum tested dosage of 100 ug, which is 20 thousand times more than the minimum effective dosage of 5 ng of native or synthetic, monomeric ST in this assay.

The instillation of 1 mg of the network polymer failed to elicit fluid secretion in ligated rat ileal loops [Klipstein, *Infect. Immun.* 40:924–929 (1983)]. That value is 5.9 million times more than the $ED_{50}$ (one-half of the dosage that yields maximum secretion) of LT [170 picograms (pg)] and 500 thousand times more than the $ED_{50}$ dosage of ST (2 ng) in this assay.

Figure 4:
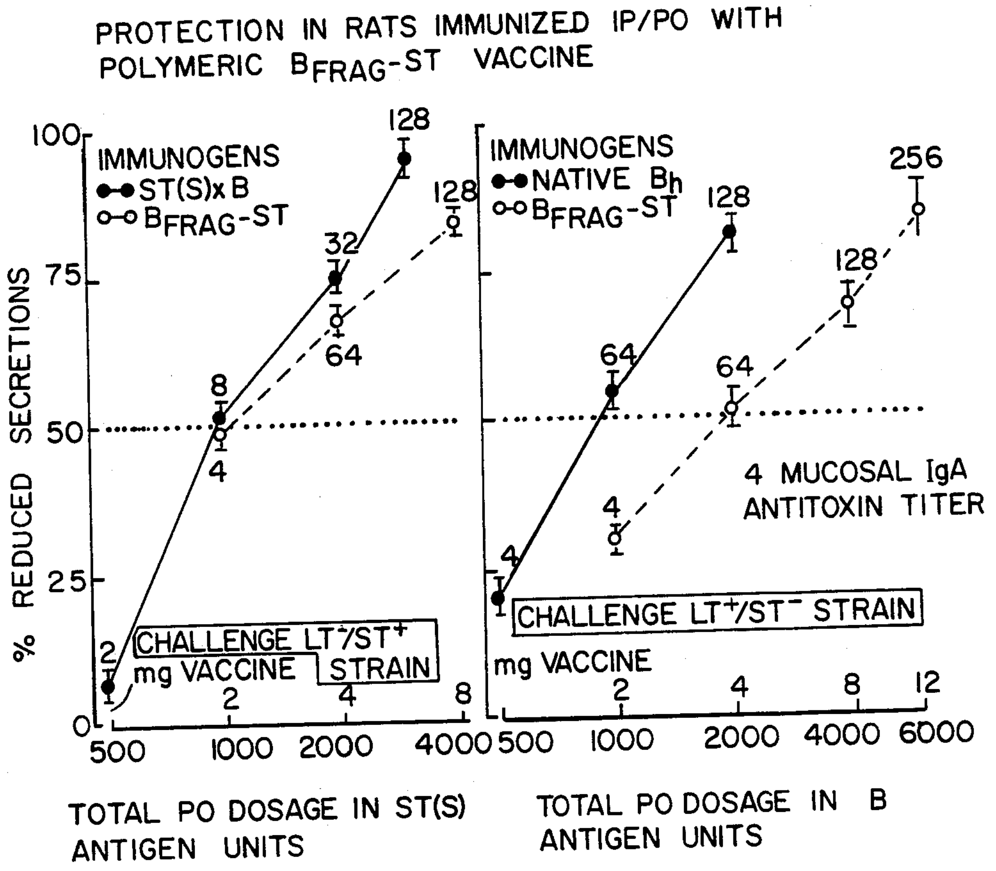

(3) Immunogenicity. The results of immunization of rats with the network polymer as an immunogen in a vaccine were compared to that achieved by immunization with either native B-subunit or synthetic ST chemically cross-linked to native B-subunit. These results are shown in FIG. 4.

Based on the ELISA determinations, the network polymer-containing vaccine was considered to contain 500 AU of both ST and B-subunit. All rats received IP primary immunization with 200 AU followed by two PO booster immunizations with graded AU dosages A total PO dosage of 4,000 ST AU of the network polymer-containing vaccine raised the same level of intestinal IgA ST antitoxin titers and provided the same degree of protection against challenge with the viable $LT/ST^+$ strain as that achieved by a total PO dosage of 3,000 ST AU in the chemically linked synthetic ST/native B-subunit conjugate [ST(S)XB]. A total PO dosage of 6,000 B-subunit AU of network polymer-containing vaccine was required, however, to yield the equivalent anti-toxin response and degree of protection against challenge with the $LT^+/ST^-$ strain as 2,000 AU of native B-subunit. These observations indicated that the immunogenicity of the ST polypeptide portion of the network polymer immunogen was approximately the same as that of synthetic ST alone, but that of the LTB polypeptide portion of the network polymer immunogen was between one-half to one-third that of the native B-subunit.

Figure 5:
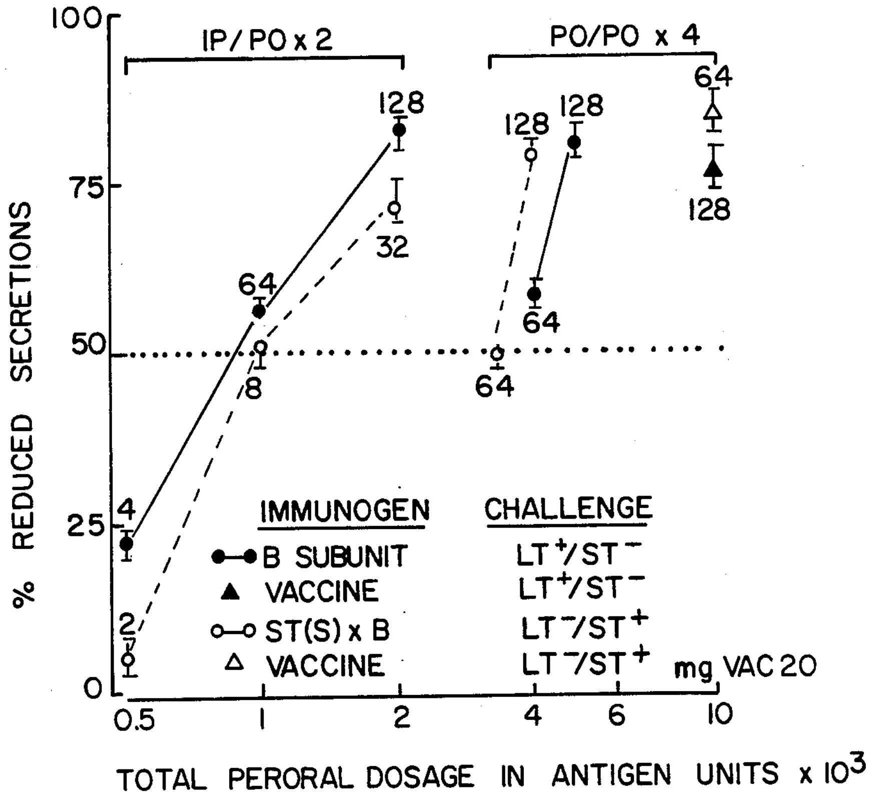
FIG. 5 is a graph (right-hand panel) illustrating the results of immunization of rats given four, weekly PO immunizations (PO/PO) of vaccines containing as active immunogen the network polymer containing the cmposite LT/ST polypeotide of FIG. 3 as repeating units [Δ and ▲; VACCINE], native $LT_h$ B-subunit [●—●; B SUBUNIT], or the before-described synthetic ST cross-linked to the native $LT_h$ B-subunit [○--○; ST(S)XB]. Challenges and the expression of results are as described for FIG. 3, with the exception that the milligrams of immunogen in the vaccines (mg VAC) are shown on the abscissa as are the number of antigen units administered.

The immunogenicity of the network polymer-containing vaccine was also assayed in rats immunized exclusively by the PO route, given on 4 weekly occasions. Rats typically differ from rabbits in that they require larger PO doses of toxins or cross-linked toxoid vaccines in the absence of parenteral primary immunization [Klipstein and Engert, *Infect. Immun.* 31:252–260 (1981); Klipstein et al., *Infect. Immun.* 40:924–929 (1983); and Klipstein et al., *Infect. Immun.* 40:888–893 (1983)]. The total PO dosage by this approach needed to raise intestinal IgA antitoxin titers to 128 and to provide strong protection in rats was 4,000 AU of synthetic ST (chemically cross-linked to native B-subunit) and 5,000 AU of B-native subunit, or roughly twice that needed by the IP/PO approach. This is shown by the data of FIG. 5.

Based on this finding, plus the fact that the immunogenicity of the LTB polypeptide portion of the network polymer was about one-half that of native B-subunit, rats were immunized with a total PO dosage of 20 mg of synthetic vaccine containing 10,000 AU of ST and B-subunit. This achieved the same anti-toxin response and degree of protection as that resulted from immunization with synthetic ST or native B-subunit.

The finding that the LTB polypeptide portion of the network polymer immunogen was less immunogenic than native B-subunit was surprising since previous results indicated that antigenicity, as determined by ELISA, closely correlates with immunogenicity as determined by the response to immunization in experimental animals [Klipstein et al., *Infect. Immun.* 40:924–929 (1983); and Klipstein et al., *Infect. Immun.* 44:268–273 (1984)]. The reasons for this discrepancy are uncertain, but it is doubted that the relatively lowered immunogenicity was due to the fact that the amino acid residue sequence of the LTB polypeptide portion of the immunogen was based on that described for porcine B-subunit [Dallas and Falkow, *Nature* 277:406–407 (1979)] whereas the immunized rats were challenged with a human LT-producing E. coli strain.

First, the amino acid residue sequence of porcine and human B-subunits differ by only six amino acids, with the only difference in the position 58 to position 83 region being at the 64 position that contains a Met in porcine and a Lys in the human B-subunit [Yamamoto et al., *J. Bacteriol.* 152:506–509 (1982)]. Second, although porcine and human LTs contain shared and distinct antigenic determinants [Honda et al., *Infect. Immun.* 34:337–340 (1981)], with the differences residing in the B-subunits [Clements, *Infect. Immun.* 38:806–809 (1982)], it was reported that immunization with either human or pocine native B-subunit provided similar degrees of protection against homologous or heterologous LT toxins and viable strains that produced those toxins [Klipstein et al., *Infect. Immun.* 40:924–929 (1983); and Klipstein et al., *Infect. Immun.* 43:811–816 (1984)].

It seems more likely that the observed discrepancy was due to other factors. One of those factors could be the configuration of the polymeric form of the synthetic vaccine; the stereochemistry of the 18 amino acid residue ST molecule profoundly affects its immunogenicity [Klipstein et al., *Infec. Immun.* 44:268–273 (1984)], and that of the B-subunit polypeptide containing amino acids from position 58 through position 83 was altered by whether it was alone or joined to ST, or whether the whole immunogen was in monomeric or polymeric form.

A second possible factor could be suboptimal solubility properties of the vaccine's immunogen. The network polymer becomes insoluble at pH values of less than 7.0, which is slightly more alkaline the duodenal, jejunal, contents in some instances.

Preliminary studies have shown that the immunogenicity of the synthetic vaccine can be enhanced by administering it concomitantly with bicarbonate in order to increase duodenal alkalinity. In addition, as discussed herein, the amino acid residue sequence of the synthetic, composite LT/ST polypeptide may be altered by the addition of acid or basic side chain-containing residues not present in LTB or ST polypeptide sequences that provide an ionic charge at the pH value of the jejunum (about pH 6.5) to assist in solubilizing the synthetic immunogen in the intestinal tract.

D. Further Antigenicitv Studies

The data in Table 1, below, illustrate antigenicities of synthetic polypeptides corresponding to portions of the LTB protein sequence of about position 35 to about position 95 from the ammino-terminus, and including the 21 residue signal peptide in the numbering. The data are for the prcine LTB polypeptides:

(a) alone; or (b) as a composite LT/ST polypeptide repeating unit of a network polymer (polymer). Antigenicities were measured using the B/B and $GM_1$/B ELISA assays for LTB polypeptides and the ST/ST ELISA assay described hereinafter in the MATERIALS AND METHODS Section.

TABLE 1

| $LT_pB$ Amino Acid Position[2] | Form | Antigenicities[1] LTB Antigenicity B/B | $GM_1$/B | ST Antigenicity |
|---|---|---|---|---|
| 37-75 | Polymer | 31 | 22 | 48 |
| 64-75 | Polymer | 32 | 25 | 48 |
| 58-83 | Alone | 21 | 27 | — |
| | Polymer[3] | 53–126 | 53–98 | — |
| 63-83 | Polymer | 52 | 47 | 53 |
| 69-83 | Polymer | 13 | 12 | 28 |
| 76-83 | Polymer | 27 | 25 | 35 |

[1]Antigenicities are expressed as the percentage of activity of native LTB-subunit or of a synthetic ST-Ibh monomer.
[2]Amino acid residue position from the amino-terminus of the $LT_p$ B-subunit protein. The amino acid residues in each polypeptide may be determined by reference to the sequence shown in FIG. 1 or Table 6 in subsection I, hereinafter.
[3]Range of ELISA-determined antigenicities for three network polymer preparations.

The above results illustrate the antigenic efficacies of a polypeptide and various network polymers containing composite LT/ST polypeptides as repeating units.

E. Immunogenicity/Antigenicity Studies

Further antigenicity studies were also carried out with antibodies raised to immunogens composed of $LT_pB$ polypeptides conjugated to tetanus toxoid (TT) an keyhole limpet hemocyanin (KLH) as carriers. Here, the immunogenic conjugates dispersed in a physiologically tolerable diluent as a vaccine were introduced in unit doses into rabbits as host animals.

The hosts were maintained for a period of time sufficient to induce antibodies to the $LT_pB$ polypeptides, a period of about 4 to about 5 weeks. The animals were then bled and the antibody-containing antiserum to the immunogenic polypeptides was obtained.

The one-half maximum binding titers for each antiserum was then assayed by ELISA using either the polypeptide immunogen or the native $LT_p$ B-subunit as antigen. Details of the procedures utilized are provided in the MATERIALS AND METHODS Section hereinafter. The results of these assays using tetanus toxoid as carrier are shown in Table 2, below.

TABLE 2

| $LT_pB$ Amino Acid Position[2] | Antigenicities of $LT_pB$ Polypeptide/Tetanus Toxoid Conjugates[1] Anti-Polypeptide Titer[3] | Anti-Native $LT_hB$ Titer[4] |
|---|---|---|
| 35-55 | 320; 1280 | 360–640 |
| 43-63 | 1280 | less than 10 |
| 48-57 | more than 1280 | 20 |

TABLE 2-continued

| Antigenicities of $LT_pB$ Polypeptide/ Tetanus Toxoid Conjugates[1] | | |
|---|---|---|
| $LT_pB$ Amino Acid Position[2] | Anti-Polypeptide Titer[3] | Anti-Native $LT_hB$ Titer[4] |
| 48-63 | more than 1280; 640 | less than 10 |
| 54-72 | more than 1280 | 40; 80-160 |
| 58-83 | 1280; more than 1280 | 320; less than 10 |
| 58-83[5] | 32,000; 2000 | 640-1280; 80-160 |
| 61-77 | 32,000 | 320-640 |
| 63-93 | 16,000; 32,000 | 800-1600 |
| 71-87 | 3200-6400; 25,000 | 160-320; 40-80 |
| 77-94 | more than 1280 | less than 10; 320 |
| 58-83/ST-Ibh[6] | more than 1280; 1280 | 160; 640-1280 |
| 48-57/ST-Ibh[6] | more than 1280; 1280 | less than 10 |

[1]Results are reported for antiserum dilutions (titers), e.g., 1:1280, at which one-half maximum binding was observed. Two rabbits were utilized for each determination. Titers separated by a semicolon (;) indicate that titers from both animals differed significantly. Titers separated by a hyphen (-) indicate that one-half maximum binding was observed between the two dilutions noted.
[2]Amino acid residue sequence corresponding to the indicated positions from the amino-terminus of the $LT_p$ B-subunit. Specific amino acid residue sequences utilized may be obtained by reference to FIG. 1 or Table 6 of subsection I, hereinafter.
[3]Antigenicity as to the polypeptide of the immunogen.
[4]Antigenicity as to the native $LT_h$ B-subunit.
[5]Repeat of the immediately preceding assay using antiserum from a second preparation of immunogen.
[6]Antigenicity of an oxidized, composite LT/ST polypeptide monomer containing the indicated $LT_pB$ polypeptide that was peptide-bonded to the amino-terminus of the 18-residue ST-Ibh polypeptide, and coupled as a conjugate to TT.

The results of Table 2 illustrate that the polypeptides and composite LT/ST polypeptides of this invention are immunogenic and are also antigenic. Those polypeptides are immunogenic in that they are capable of inducing the production of antibodies that immunoreact with (bind to) the native $LT_h$ B-subunit protein. The polypeptides are antigenic in that they immunoreact with antibodies that they have induced.

A similar study was carried out using conjugates containing KLH as carrier for the composite LT/ST polypeptide but using only one rabbit as the host mammal. The results of that study are shown in Table 3, below.

TABLE 3

| Antigenicities of $LT_pB$ Polypeptide/ KLH Conjugate[1] | | |
|---|---|---|
| $LT_pB$ Amino Acid Position[2] | Anti-Polypeptide Titer[3] | Anti-Native $LT_hB$ Titer[4] |
| 35-55 | 32,000-64,000 | 8000 |
| 48-57 | 640 | 20-40 |
| 48-63 | 16,000-32,000 | 20-40 |
| 54-72 | 8,000-16,000 | 20-40 |
| 58-83 | 4,000-8,000 | 80 |
| 58-83[5] | 4,000-8,000 | 80 |
| 61-77 | 16,000-32,000 | 40-80 |
| 63-93 | 16,000-32,000 | 80-160 |
| 71-87 | 32,000-64,000 | 80-160 |
| 77-94 | 32,000-64,000 | 40-80 |

[1-5] See Notes 1-5 of Table 2.

As is seen from the results above, use of KLH as a carrier as compared to TT improves the antigenicity of the antibodies induced for the immunizing polypeptide, while reducing the antigenicity of the antibodies toward the native $LT_h$ B-subunit.

It is noted that the results in Tables 2 and 3 differ from those shown in Table 1 or in FIG. 2 in an important way, The results of Table 2 and 3 show a direct interaction between antibodies induced by the polypeptide conjugate and composite LT/ST polypeptide conjugates of this invention with the native $LT_h$ B-subunit protein molecule. The antigenicities illustrated in Table 1 and FIG. 2 show the immunoreactivity of antibodies raised against the native $LT_h$ B-subunit protein with a polypeptide or composite LT/ST polypeptide.

It is known that antibodies raised to an intact protein frequently do not bind to polypeptides that correspond in amino acid residue sequence to antigenic determinants of the protein. See, for example, Shinnick et al., *Ann. Rev. Microbiol.* 37:425-446 (1983). Thus, a failure to exhibit binding, or a low binding titer in the $GM_1$/B or B/B ELISA studies may indicate only that antibodies induced by the whole, native $LT_h$ B-subunit do not recognize a polypeptide or composite LT/ST polypeptide of this invention.

Details of the immunization regimens and ELISA studies are provided in the MATERIALS AND METHODS Section.

F. Vaccine Reproducability

A further study was undertaken to assess the reproducability of results obtained using vaccines prepared using a network polymer of this invention dispersed in a physiologically tolerable diluent. The network polymers utilized were two preparations of polymer containing a plurality of composite LT/ST polypeptides bonded together with intramolecular, interpolypeptide cystine disulfide bonds provided by the Cys residues of ST Ibh polypeptide sequence portions of the composite. The LT polypeptide portion of the composite LT/ST polypeptide corresponded in sequence to postions 58 through 83 of the $LT_p$ B-subunit.

Results for one polymer preparation and vaccine, referred to hereinbelow as Lot 001, are discussed in Section C, hereinbefore, and are shown in FIGS. 4 and 5. That material was also referred to hereinbefore in FIGS. 4 and 5 as the $B_{FRAG}$-ST vaccine. The second preparation of that polymeric immunogen is referred to hereinbelow as Lot 002. That lot exhibited antigenicities of 53 and 53 percents of native LTB antigenicity by the B/B and $GM_1$/B assays, and 48 percent of ST antigenicity by the ST/ST assay.

The lack of toxicity exhibited by Lot 001 was discussed before. Lot 002 exhibited a negative response in the suckling mouse assay at a dosage of 100 micrograms in each of three mice. Lot 002 failed to induce fluid secretion in rat ligated illeal loops at a dose of 1000 micrograms in each of two rats. Both preparations therefore showed substantially no biological activity.

Vaccines prepared containing each of Lot 001 and Lot 002 were used to immunize rats. The immunization regimen utilized a priming parenteral injection of 600 micrograms of immunogen in the vaccine followed by two PO boosts of 4 milligrams each of each of the two lots.

When assayed for mean intestinal IgA, the host animals' antitoxin titers were 64 against ST and 128 against the LT B-subunit for both vaccines. Protection of the thus immunized rats against challenge with viable ETEC strains producing either ST ($ST^+/LT^-$) or LT ($ST^-/LT^+$) enterotoxin are shown in Table 4, below.

TABLE 4

| Challenge With Enterotoxin-Producing *E. coli* | | |
|---|---|---|
| | Protection Against[1] | |
| Lot # | $ST^+/LT^-$ | $ST^-/LT^+$ |
| 001 | 84 ± 2 | 69 ± 1 |

TABLE 4-continued

| | Challenge With Enterotoxin-Producing *E. coli* Protection Against[1] | |
|---|---|---|
| Lot # | $ST^+/LT^-$ | $ST^-/LT^+$ |
| 002 | 79 ± 2 | 72 ± 3 |

[1]Values are as a percentage of reduced secretion in immunized rats as compared to unimmunized, challenged control rats.

As can be seen from the data in Table 4, the vaccines were substantially identical in reducing secretion and in protecting the immunized host animals from the challenging strains of *E. coli.*

The vaccine prepared from network polymer Lot 002 was also administered at a higher level than would normally be utilized to ascertain whether any adverse side effects would be observed in host animals. Here, intraperitoneal injections of 15 milligrams were given to each of two guinea pigs weighing 200–250 grams each and to each of two mice weighing 12–15 grams. The weights and general conditions of the animals were studied over a seven day time period. The guinea pigs gained 40.1 and 47.6 grams while the mice gained 5.3 and 8.8 grams. No adverse side effects were observed in any of the animals.

G. Antigenicity/Immunogenicity with Varied LT Polypeptide Chain Length

Yet another study was carried out using a series of composite LT/ST polypeptide coupled to tetanus toxoid (TT) as carrier to assess the effect of the polypeptide chain length of the LTB polypeptide portion of a composite LT/ST polypeptide; the LTB polypeptide being from the region of position 58 through 83 of the LT B-subunit, including the 21 residue signal peptide sequence. These studies were conducted as described before in Section VI E, and in Table 2. The results are shown in Table 5, below.

TABLE 5

| | Antigenicities of $LT_{58\text{-}83}$/ST/TT Conjugates[1] | | |
|---|---|---|---|
| $LT_pB$ Amino Acid Position[2] | Anti-Composite Titer[3] | Anti-Native $LT_pB$ Titer[4] | Anti-$LT_{58\text{-}83}$ Titer[6] |
| 58-83/ST | 16,000–32,000 | — | 8,000–16,000 |
| 58-83/ST[5] | 12,800 | 60–80 | 8,000–16,000 |
| 61-83/ST | 6,400 | 80–160 | 3,200–6,400 |
| 63-83/ST | 6,400–12,800 | 80–160 | 3,200–6,400 |
| 69-83/ST | 6,400–12,800 | 60–80 | 400–800 |
| 73-83/ST | 6,400–12,800 | 60–80 | 200–400 |
| 58-83[7] | — | — | 16,000–32,000 |
| LTB | 1,600–3,200 | 64,000 | 640–1,280 |

[1-4]See Notes 1–4 of Table 2.
[5]A second preparation of the composite LT/ST polypeptide.
[6]Titer against the free polypeptide corresponding to positions 58-83 of $LT_pB$.
[7]An LTB polypeptide corresponding to positions 58-83 without the ST polypeptide portion was used conjugated to TT.
[8]$LT_h$ B-subunit used as a whole molecule immunogen.

The above results illustrate that all of the examined composite LT/ST polypeptides containing 11 through 36 residues and having amino acid residue sequences that correspond to positions 58 through 83 of the LT polypeptide portion were similarly effective immunogens in inducing antibodies that immunoreact with the native $LT_h$ B-subunit.

Immunoreactions of antibodies induced by the above composite LT/ST polypeptide conjugates were also assayed against ST Ibh and ST Ibp. Although the ST polypeptide portions of the composites remained the same, improved titers were also observed with composite LT/ST polypeptides containing about 20–25 residues in the LT polypeptide portions. The antibodies induced immunoreacted with both ST Ibh and ST Ibp, with the titers against ST Ibh being several times larger than against ST Ibp.

H. Additional Polypeptides

A composite LT/ST polypeptide was prepared that contained the residues of position 48 through position 57 (numbered to include the signal peptide) of the $LT_p$ B-subunit peptide bonded to the amino-terminus of ST Ibh. (The position numbers of this polypeptide correspond to position 27 through position 36 if the signal peptide amino acid residues are not included.) The polypeptide was then oxidized at concentrations of 0.1 mg/ml, 1.0 mg/ml and 5.0 mg/ml in 0.5M ammonium bicarbonate buffer using duplicate oxidation procedures, and at concentrations of 0.1 mg/ml and 0.2 mg/ml in 0.1 M ammonium acetate at pH 8.

The 0.1 and 0.2 mg/ml concentrations are believed to contain mostly monomeric composite LT/ST polypeptides. The oxidation at 1.0 mg/ml is believed to provide mostly network polymer containing the composite LT/ST polypeptide as repeating units. The 5.0 mg/ml preparation contained substantially only polymer.

Antigenicites assayed using the ST/ST assay discussed in the MATERIALS AND METHODS Section provided antigenicities of: (a) 31.5 and 68.1 percents for the 0.1 mg/ml oxidations in ammonium bicarbonate buffer; 32.9 and 41.9 percents for oxidations at 0.1 and 0.2 mg/ml, respectively, in the ammonium acetate buffer; (c) 103.3 and 350.0 percents for the 1.0 mg/ml oxidations in ammonium bicarbonate; and (d) 98.4 and 262.5 percents for the 5.0 mg/ml oxidations in ammonium bicarbonate. Percentages were based upon the antigenicity exhibited by monomeric ST Ibh polypeptides that have an antigenicity substantially similar to that of native ST Ibp.

A similar study was carried out using another composite LT/ST polypeptide. The sequence of that polypeptide corresponded to positions 58 through 83 (including the signal peptide) of the $LT_p$ B-subunit peptide bonded directly to the amino terminus of ST Ibh. (The sequence positions of this polypeptide correspond to position 37 through 62 without the signal peptide residues.)

Oxidations in ambient air, as above, were carried out at 0.185 mg/ml, 0.25 mg/ml, 0.50 mg/ml and at 0.523 mg/ml in 0.5 M ammonium bicarbonate. Oxidations were also carried out at 0.25 mg/ml and 1.25 mg/ml in 0.1 M ammonium acetate at pH 8.0. Antigenicities, measured as described above, were 205, 446, 208, 236, 42 and 13 percents, respectively.

The results of the above two studies illustrate the usefulness of all of the oxidizing conditions studied. Those results also indicate that materials with improved antigenicities resulted from oxidations in ammonium bicarbonate as compared to ammonium acetate as an oxidation buffer system.

Composite LT/ST polypeptides containing an LTB polypeptide corresponding in amino acid residue sequence to positions 35 through 55 of the $LT_p$ B-subunit peptide-bonded directly to the carboxy-terminus of an ST Ibh polypeptide, and corresponding in sequence to positions 58 through 83 of the $LT_p$ B-subunit peptide bonded to the amino-terminus of an ST Ibh polypeptide and further including two additional Lys residues peptide-bonded at the amino-terminus of the LTB polypeptide were also prepared.

The first-named of those polypeptides (ST-$LT_{35-55}$) thus conforms to a compound of Formula VII wherein:

"n", "o", "r", "s" and "m" are zero;

"p" is one;

B is a polypeptide that contains 18 amino acid residues corresponding in sequence to the carboxy-terminal 18 residues of a heat-stable enterotoxin of *Escherichia coli;* i.e., the ST Ibh polypeptide; and A is a polypeptide that contains 21 amino acid residues corresponding in sequence to the amino acid residue sequence of positions 35 through 55 from the amino-terminus of the B-subunit of the heat-labile enterotoxin of *Escherichia coli,* including the signal polypeptide; i.e., the $LT_p$ B-subunit.

The second of those polypeptides (LysLys$LT_{57-83}$-ST) conforms to a compound of Formula VII wherein:

"n" is 2;

"p" is 1;

"r", "s", "o" and "m" are zero;

X is Lys;

Y and Z are absent;

A is a polypeptide containing 27 amino acid residues corresponding in sequence to the sequence of position 58 through position 83 from the amino-terminus of the B-subunit of the heat-labile enterotoxine of *E. coli,* including the signal peptide; and B is the ST polypeptide discussed immediately above.

Initial studies with a network polymer having a plurality of LysLys$LT_{58-83}$—ST repeating units indicated that solubility was improved over similarly prepared polymers prepared from a composite LT/ST polypeptide having the same sequence of LTB and ST polypeptides but lacking the additional Lys residues; immunoreactivities for the two polymers were substantially similar.

The remaining composite LT/ST polypeptides for which specific results as conjugates or as repeating units of network polymers are discussed herein conform to compounds of Formula VII wherein:

"n", "r", "s", "p" and "m" are zero:

X,Y and Z are absent;

"o" is one;

A is a polypeptide that contains 8–31 amino acid residues corresponding to the amino acid residue sequence of about position 35 to about position 95 from the amino-terminus of the B-subunit of the heat-labile enterotoxin of *E. coli,* wherein the position numbers include the 21 residue signal peptide; and B is a polypeptide that contains 18 amino acid residues corresponding in sequence to the carboxy-terminal 18 residues of a heat-stable enterotoxin of *E. coli,* as before discussed.

I. Seouences of Prepared LTB Polvpeptides

Table 6, below, provides sequences of LTB-containing polypeptides referred to herein. Each polypeptide is listed by an abbreviation that indicates subscript sequence position numbers counted from the amino-terminus of the LT B-subunit, including the 21 residue signal peptide, and whether the polypeptide sequence corresponds to only a LTB polypeptide or to a composite LT/ST polypeptide. A composite LT/ST polypeptide having an LTB polypeptide at the amino-terminus is indicated by the abbreviation $LT_{subscript}$--ST, while a polypeptide having an ST polypeptide at the amino-terminus is abbreviated ST--$LT_{subscript}$. The amino acid residue sequence corresponding to each abbreviation is shown to the right of the abbreviation and is written from left to right and in the direction from amino-terminus to carboxy-terminus. Each ST polypeptide sequence shown below is that of ST Ibh.

TABLE 6

Prepared LBT Polypeptides

| LTB Sequence Position | Polypeptide Sequence |
|---|---|
| LTB Polypeptides | |
| $LTB_{35-55}$ | AsnThrGlnIleTyrThrIleAsnAspLysIleLeuSerTyrThrGluSerMetAlaGlyLys |
| $LTB_{43-63}$ | AspLysIleLeuSerTyrThrGluSerMetAlaGlyLysArgGluMetValIleIleThrPhe |
| $LTB_{48-57}$ | TyrThrGluSerMetAlaGlyLysArgGlu |
| $LTB_{48-63}$ | TyrThrGluSerMetAlaGlyLysArgGluMetValIleIleThrPhe |
| $LTB_{54-72}$ | GlyLysArgGluMetValIleIleThrPheMetSerGlyGluThrPheGlnValGlu |
| $LTB_{58-83}$ | MetValIleIleThrPheMetSerGlyGluThrPheGlnValGluValProGlySerGlnHisIleAspSerGlnLys |
| $LTB_{61-77}$ | IleThrPheMetSerGlyGluThrPheGlnValGluValProGlySerGln |
| $LTB_{63-93}$ | PheMetSerGlyGluThrPheGlnValGluValProGlySerGlnHisIleAspSerGlnLysLysAlaIleGluArgMetLysAspThrLeu |
| $LTB_{71-87}$ | ValGluValProGlySerGlnHisIleAspSerGlnLysLysAlaIleGlu |
| $LTB_{77-94}$ | GlnHisIleAspSerGlnLysLysAlaIleGluArgMetLysAspThrLeuArg |
| diCys-$LT_{58-83}$ | CysMetValIleIleThrPheMetSerGlyGluThrPheGlnValGluValProGlySerGlnHisIleAspSerGlnLysCys |
| Composite LT/ST Polypeptides | |
| $LTB_{35-55}$-ST | AsnThrGlnIleTyrThrIleAsnAspLysIleLeuSerTyrThrGluSerMetAlaGlyLysAsnThrPheTyrCysCysGluLeuCysCysTyrProAlaCysAlaGlyCysAsn |
| $LTB_{37-75}$-ST | GlnIleTyrThrIleAsnAspLysIleLeuSerTyrThrGluSerMetAlaGlyLysArgGluMetValIleIleThrPheMetSerGlyGluThrPheGlnValGluValProGlyAsnThrPheTyrCysCysGluLeuCysCysTyrProAlaCysAlaGlyCysAsn |
| $LT_{48-57}$-ST | TyrThrGluSerMetAlaGlyLysAsnThrPheTyrCysCysGluLeuCysCysTyrProAlaCysAlaGlyCysAsn |
| $LT_{58-83}$-ST | MetValIleIleThrPheMetSerGlyGluThrPheGlnValGluValProGlySerGlnHisIleAspSerGlnLysAsnThrPheTyrCysCysGluLeuCysCysTyrProAlaCysAlaGlyCysAsn |
| $LT_{LysLys58-83}$-ST | LysLysMetValIleIleThrPheMetSerGlyGluThrPheGlnValGluValProGlySerGlnHisIleAspSerGlnLysAsnThrPheTyrCysCysGluLeuCysCysTyrProAlaCysAlaGlyCysAsn |
| $LT_{64-75}$-ST | MetSerGlyGluThrPheGlnValGluValProGlyAsnThrPheTyrCysCysGluLeuCysCysTyrProAlaCysAlaGlyCysAsn |
| $LT_{63-83}$-ST | PheMetSerGlyGluThrPheGlnValGluValProGlySerGlnHisIleAspSerGlnLysAsnThrPheTyrCysCysGluLeuCysCysTyrProAlaCysAlaGlyCysAsn |
| $LT_{69-83}$-ST | PheGlnValGluValProGlySerGlnHisIleAspSerGlnLysAsnThrPheTyrCysCysGluLeuCysCysTyrProAlaCysAlaGlyCysAsn |
| $LT_{76-83}$-ST | SerGlnHisIleAspSerGlnLysAsnThrPheTyrCysCysGluLeuCysCysTyrProAlaCysAlaGlyCysAsn |
| ST-$LT_{35-55}$ | AsnThrPheTyrCysCysGluLeuCysCysTyrProAlaCysAlaGlyCysAsnAsnThrGlnIleTyrThrIleAsnAspLysIle |

TABLE 6-continued

| Prepared LBT Polypeptides | |
| --- | --- |
| LTB Sequence Position | Polypeptide Sequence |
| | LeuSerTyrThrGluSerMetAlaGlyLys |

VII. MATERIALS AND METHODS

A. Enterotoxin production

Native LT toxin B-subunit was purified by chromatographic techniques [Clements et al. *Infect. Immun.* 29:91–97 (1980)] from batch cultures of *E. coli* strain pDF 87, a transformed K-12 derivative bearing the B-subunit plasmid of human *E. coli* strain H-10407 [Clements et al., *Infect. Immun.* 40:653–658 (1983)]. Synthetic ST Ibh whose sequence is based on the 18 amino acid residue sequence described by Chan and Gianella for human ST [Chan and Giannella, *J. Biol. Chem.* 256:7744–7746 (1981)] was prepared as described herein by solid phase techniques; this polypeptide alone and unlinked to an LTB polypeptide has the same biological properties and immunogenicity as native ST but differs in thin layer chromatographic and electrophoretic properties. Additional synthetic ST-containing molecules were prepared by similar techniques. The synthetic ST was chemically cross-linked to native B-subunit using a water soluble carbodiimide for the conjugating reagent as described in Klipstein et al. *J. Infect. Dis.* 147:318-326 (1983). The amounts of native and synthetic immunogen used in vaccines were based on their protein concentrations determined by the method of Lowry et al., *J. Biol. Chem.* 193:265–275 (1951).

B. Synthesis of Polypeptides

Polypeptides were made including different lengths of amino acid residues from various regions in the porcine heat-labile enterotoxin B-subunit (LTp B) sequence described by Dallas and Falkow, *Nature* 288:499–501 (1980). These polypeptides were prepared either individually or synthesized onto the amino- or carboxy-terminal ends of an ST amino acid residue sequence to form a composite LT/ST polypeptide.

Polypeptides were made by the solid phase methods described generally in Houghten et al., *Int. J. Pept. Prot. Res.* 16:311-320 (1980) and Merrifield, *J. Am. Chem. Soc.* 85:2149–2154 (1983), and modified as described herein. A Sam II automated peptide synthesizer (Biosearch Inc., San Raphael, Calif.) or a Beckman Model 990B peptide synthesizer (Beckman Instruments Co., Berkeley, Calif.) was used for the synthesis.

The following discussion relates particularly to the preparation of composite LT/ST polypeptides as the synthesis of such polypeptides also describes the procedures for LTB polypeptides that are not portions of a composite LT/ST polypeptide. DiCys-polypeptides were also prepared as described below, except that blocked Cys residues were the first and last residues of the polypeptides.

Typically, the syntheses began with benzhydryl amine resin (0.57 miliequivalents per gram; meq/g) to which was coupled a protected carboxy-terminal amino acid residue of a particular sequence such as alpha-O-benzyl-BOC-aspartic acid as to provide the carboxy-terminal ST asparagine upon cleavage with hydrogen fluoride. This and subsequent couplings were carried out with a 10 fold molar excess of amino-terminal amine protected amino acid (N-t-butyl-oxycarbonyl; BOC) using dicyclohexlcarbodiimide as the coupling, peptide bond-forming reagent. A two molar excess of both reagents may also be used.

Usually used amino acid side chain protecting groups were utilized, and are as follows: O-(p-bromobenzyloxycarbonyl) for tyrosine and lysine, O-benzyl for threonine, benzyl ester for glutamic acid and aspartic acid, S-methoxybenzyl for cysteine, dinitrophenyl for histidine and tosyl for arginine, when present.

For couplings involving protected asparagine, an equimolar amount of N-hydroxy-benzotriazole was added to the reaction mixture and dimethyl formamide (DMF) was used as solvent. Couplings were found to be typically more than 99% complete by the picric acid test of Gisin *Anal. Chem. Act.* 58:298–249 (1972). Protected amino acids were recrystallized from appropriate solvents prior to use to give single spots by thin layer chromatography. The histidine protecting group was removed prior to cleavage from the resin by thiolytic cleavage with 1% thiophenol in DMF. The amino-terminal BOC group was also removed prior to cleavage from the resin with a final trifluoroacetic acid deprotection step to prevent acetylation of methionine during the hydrogen fluoride cleavage procedure.

The blocked amino acids were coupled serially to the resin. The amino-terminal BOC group of the last coupled amino acid was removed prior to the addition of the next blocked polypeptide until the desired polypeptide was synthesized linked (bound) to the resin. The resin-bound polypeptide was then cleaved to provide the resin and polypeptide.

Cleavage of polypeptides from their resins and removal of the remaining protecting groups was accomplished by treating the polypeptide-resin [0.5 grams (g)] with 0.5 milliliters (ml) of anisole and 20 ml of anhydrous hydrogen fluoride (or by treating the polypeptide-resin with twice its weight of anisole and 40 times its volume relative to weight of anhydrous hydrogen fluoride) at 4° C. for 1 hour. After evaporating the hydrogen fluoride initially with a stream of $N_2$ and finally with aspiration, the residue was extracted with anydrous ether three times to remove the anisole, and was dried under aspiration followed by vacuum.

The vacuum-dried material was first extracted with 5% aqueous acetic acid (3 times 50 ml each) followed by extractions using 50% aqueous acetic acid (4 times 50 ml). The first extraction removed low molecular weight polypeptides and tyrosine that was used in some preparations to protect the Cys mercaptan groups. The second extraction separated the free polypeptide from the resin. After dilution with water to a concentration of 10–20% acetic acid, the resulting solution was lyophilized to provide a monomeric unoxidized, first polypeptide.

The crude polypeptides were admixed with a 3-fold molar excess of dithiothreitol to maintain their reduced state, and were partially purified by Sephadex G-50 gel filtration (Pharmacia Fine Chemicals, Piscataway, N.J.) with 0.1 molar (M) ammonium bicarbonate (pH 8.0) as the eluent. The first fraction in the void volume of the column (63% by weight of one preparation) was lyophilized or used immediately after collection in order to prevent uncontrolled oxidation when sulfhydryl groups were present. The amino acid composition of such materials were confirmed and found to be ±10 percent of theory.

Preparations of synthetic LTB polypeptides not bonded to a synthetic ST polypeptide were typically utilized after the above gel filtration purification. Preparations of composite LT/ST polypeptides were further treated as described below.

In one preparation, a 44 amino acid residue composite LT/ST polypeptide sequence containing B-subunit residues 58 through 83 was prepared joined directly to a synthetic 18 amino acid residue sequence of ST by a peptide bond between the carboxy-terminal Lys residue of LTB residue 83 and the amino-terminal Asn residue of the synthetic ST portion. That monomeric composite LT/ST polypeptide, used as a repeating unit, was oxidized by contacting molecular oxygen ($O_2$) present in ambient air with an aqueous oxidation medium containing the reduced LT/ST composite polypeptide typically present at 1.0 milligram (mg) per ml in 0.1 M ammonium bicarbonate (pH 8.0) with slow stirring at 22° C. for 20 hours to form a network polymer having composite LT/ST polypeptide repeating units bonded together by interpolypeptide cystine disulfide bonds. Free sulfhydryl groups were negligable as determined by the Ellman reaction [Ellman *Arch. Biochem. Biophys.* 82:70–77 (1959)]. Network polymers containing other LT polypeptide sequences were prepared similarly unless otherwise stated. Preparations of composite LT/ST polypeptides to form oxidized monomers were typically carried out at 0.1 to 0.25 mg/ml using otherwise similar oxidation conditions.

Oxidations to form useful monomeric and network polymeric composite LT/ST polypeptides have also been carried out using 0.5 M ammonium carbonate and 0.1 M ammonium acetate. The pH value of the oxidizing media has also been varied between pH 6.0 and 10.0.

Partial purification of this polymeric material was effected by passage through a Sephadex G-50 (Pharmacia) column equilibrated with 0.1 M ammonium bicarbonate (pH 8.0). The void volumn was collected and lyophylized. A sizing column of Sephacryl S-200 (Pharmacia) showed a single peak for one network polymer so prepared with a molecular weight of approximately 22,000 daltons.

C. Assays for Toxic Properties

The toxic properties of the network polymer immunogen discussed in Section VI C(2) were tested by (i) Chinese hamster ovary (CHO) tissue culture assay for LT activity [Guerrant et al. *Infect. Immun.* 10:320–327 (1974)], (ii) the suckling mouse assay for ST secretory activity [Giannella, *Infect. Immun.* 14–95–99 (1976)], and (iii) instillation into rat ligated ileal loops for secretory activity [Klipstein et al. *Infect. Immun.* 40:924–929 (1983)].

D. Assay for Antigenicity

The antigenicity of the synthetic polypeptides was determined by double sandwich enzyme-linked immunosorbant assays (ELISAs) using, for the solid phase/second antibody, either $GM_1$ ganglioside (Sigma Chemical Co., St. Louis, Mo.)/anti-LT B-subunit hyperimmune antiserum ($GM_1$/B), or double species hyperimmune antisera to B-subunit (B/B), and double species hyperimmune antisera to synthetic ST (ST/ST) as described previously [Klipstein et al. *J. Infect. Dis.* 147:318–326 (1983) and Klipstein et al. *Infec. Immun.* 44:268–273 (1984)].

Briefly, antibody from one animal species raised to LTB or ST, or the ganglioside was adsorbed onto a microtiter plate well as a solid support, and any excess, unbound material was removed. An appropriate antigen (LT polypeptide, ST or LTB) was then admixed with the solid support, maintained in contact for a time sufficient for binding to occur between the antibody or ganglioside and the antigen, and any excess, unbound antigen was removed, by rinsing. Thereafter, an antibody from a second animal species (or a first species for the $GM_1$/B assay) raised to LTB or ST, as appropriate, was admixed with the solid support-bound antigen. After maintaining the admixiture for a time sufficient for the admixed antibody to immunoreact, any excess un-immunoreacted antibody was removed by rinsing. The amount of the last added antibody that immunoreacted with the solid support-bound antigen was then determined, and a comparison was made between the binding of that last added antibody to the studied polypeptide and to the control antigen, e.g., native LT B-subunit.

E. Conjugates of LT and Composite LT/ST Polypeptides Coupled to Tetanus Toxoid as Carrier Composite LT/ST polypeptide preparations were weighed out and admixed with an equal amount of tetanus toxoid (TT). The polypeptide and TT were dissolved in phosphate-buffered saline (PBS) (pH 7.2), and diluted to a final concentratron of 2 mg/ml of carrier.

The glutaraldehyde cross-linking agent (GA) was prepared initially as a 25 percent stock solution. 200 Microliters of the stock solution were admixed with 13 ml of PBS to form a working GA solution. The working GA solution was kept chilled. The working solution was admixed in an amount of 124 microliters (u/l) per one ml of carrier-polypeptide solution.

The GA working solution/carrier-polypeptide solution admixtures were stirred for about 18 hours (hr) at ambient, room temperature. That reaction mixture was thereafter dialyzed against distilled or deionized water for 6 hr, and was then lyophilized.

The dried, lyophilized material is presumed from experience to include 90 percent recovery of the carrier. The coupled, cross-linked polypeptide typically constitutes about 40 percent by weight of the total recovered material. Similar preparations are described in Klipstein et al., *J. Infect. Dis.* 147:318–326 (1983).

F. Conjugates of LT and Composite LT/ST Polypeptides Coupled to Keyhole Limpet Hemocyanin as Carrier The LTB polypeptides of Table 2 were also coupled to keyhole limpet hemocyanin (KLH) as a carrier to form conjugates. An amino-terminal Cys residue was added to those polypetides whose sequences did not contain such a residue.

KLH was dialysed against 10 mM phosphate buffer (pH 7.2) and its concentration was adjusted to 20 mg/ml prior to use. Solutions of polypeptides to be coupled were prepared at a concentration of 5 mg/ml. Coupling concentrations of 4 mg KLH to 5 mg of polypeptide were utilized.

A desired volume of the above KLH solution was selected and 55 u/l of the above phosphate buffer were added per 4 mg of KLH. A solution containing m-maleimidobenzoyl N-hydroxysuccinimide ester (MBS) dissolved at 6 mg/ml in DMF was then added at a volume of 85 u/l per 4 mg of KLH to provide a MBS:KLH molar ratio of 40:1. The resulting reaction mixture was then stirred for a time of 30 minutes at ambient, room temperature.

After the 30 minutes had elapsed, the reaction solution was run through a Sephadex G-25 (Pharmacia) column containing a bed volume of about 15 ml. The buffer used for preparation of the column was 50 mM phosphate a pH value of 6.0.

One ml fractions were collected from the eluting column. Each fraction was read at a light wavelength of 280 nanometers to ascertain the fractions in which the resulting MBS-activated KLH (KLH-MB) were located. The KLH-MB-containing fractions were then pooled. A recovery of 80 weight percent of KLH-MB is presumed in this procedure.

The collected, pooled KLH-MB-containing solution was then used as a stock solution that was utilized for coupling to each of the polypeptides. An amount of the before-discussed polypeptide-containing solution (5 mg/ml) was added to an amount of the recovered KLH-MB-containing solution to provide reaction mixtures that contained 4 mg of the KLH-MB.

The pH value of the reaction mixtures were adjusted to 7.0–7.5 with NaOH or HCl as appropriate, and were then stirred at ambient, room temperature for a time period of three hours. Thereafter, the reaction solutions were frozen and stored frozen until used.

G. Polypeptide Conjugates as Immunogens and Antiqens

Immunization and ELISA protocols utilized in relation to the material and results of Tables 2 and 3 were as follows.

Rabbits were injected subcutaneously (SQ) on day zero with a vaccine that contained 1 mg of an above prepared TT or KLH conjugate dispersed in approximately 0.75 milliliters of complete Freund's adjuvant (CFA) and 0.75 milliliter of phosphate-buffered saline (PBS) having a pH value of 7.2. The animals received booster SQ injections of a vaccine that contained the same amount of conjugated polypeptide or composite LT/ST polypeptides contained in 0.75 milliliters of incomplete Freund's adjuvant plus 0.75 milliliters of PBS on day 14, followed by a second intraperitoneal (IP) booster injection of the second-named vaccine on day 21. Serum samples from the immunized rabbits were obtained from the ear vein on days 28 and 35 after the first immunization.

Two rabbits were used for each TT conjugate, while one rabbit was used for each KLH conjugate determination.

The native $LT_h$ B-subunit antigen was dissolved in a TEAN buffer (Tris, EDTA, sodium azide, sodium chloride) at pH 4.0 to provide a stock solution containing 1 mg/ml. That stock solution was then diluted with a carbonate/bicarbonate buffer having a pH value of 8.0 to provide a second stock solution containing native $LT_h$ B-subunit at a concentration of 10 picomoles/50 ul.

50 Microliters of the second stock solution were placed into the wells of a microtiter plate, to provide 10 picomoles of the antigen to each well. The plate was then incubated in a moist chamber for a period of 18 hours at ambient, room temperature.

The wells were then washed three times with a PBS solution that contained 0.07 percent Polysorbate 20 (TWEEN® 20; ICI United States, Inc., Wilmington, DE), followed by two washes with deionized water. 100 Microliters of 1 percent bovine serum albumin (BSA) in PBS (1% BSA/PBS) were then added to each well to block sites of non-specific binding, and the BSA-containing solutions were maintained (incubated) in the wells for 1 hour at 37° C.

Solutions containing unbound BSA were shaken from the plate. Without first drying the plate, 90 ul of 1% BSA/PBS were added to each well of the top row of wells, while 50 ul of 1% BSA/PBS were added to each well of the remainder of the plate. Thereafter, 10 microliters of anitserum were added to each of the top row of wells, and the admixture so made was mixed. 50 Microliters of antiserum-containing solution from each well in the top row were then added and mixed with the 50 ul of 1% BSA/PBS in the well therebelow to provide further two-fold dilutions. Similar serial two-fold dilutions were continued for the remaining wells of the plate. After all of the dilutions had been made, the diluted antiserum-containing wells were incubated at 37° C. for a period of 1 hour. The liquid in the wells was thereafter removed and the wells were rinsed as beforedescribed.

Goat anti-rabbit serum labeled with peroxidase (Zymed Laboratories, Burlingame CA) was diluted 1:3000 by volume with 1% BSA/PBS. 50 Microliters of the resulting diluted antibody-containing solution were added to each well. The wells so prepared were maintained (incubated) for a period of 1 hour at 37° C., and were then washed as described before.

A solution of ortho-phenylenediamine (OPD) was prepared by dissolving one tablet of OPD Substrate (Pittman-Moore, Inc., Washington Crossing, NJ) in 6 milliliters of deionized water to which one drop of 3 percent hydrogen peroxide was also added. 100 Microliters of the resulting solution were added to each of the microtiter plate wells. Color development in the wells was developed at ambient, room temperature, and was stopped after 20 minutes by the addition of 25 microliters of 4 normal sulfuric acid to each well. The amount of color present in each well was determined by measuring the optical density of the liquid therein at 492 nanometers.

The amount of antibody in the rabbit serum required to saturate one-half of the LTB antigen on the plate was thereafter calculated using standard techniques.

H. Immunization procedures

Immunization procedures for the data shown in FIGS. 3–5 were as follows: Sprague-Dawley rats (150 to 175 g) were given primary immunization intraperitoneally (IP) using Freund's complete adjuvant followed by two booster immunizations given perorally (PO) at 4-day intervals. Immunization PO was given via an intragastric tube 2 hours after the PO administration of cimetidine (TAGAMET®; Smith Kline & French Laboratories, Carolina, P.R.) at a dosage of 50 milligrams/kilogram (mg/kg) body weight to ablate gastric acid secretion.

Dosages of the chemically cross-linked ST-B-subunit conjugate and of the network polymer containing composite LT/ST polypeptide repeating units are expressed in antigen units (AU) per mg. Such dosages (in AU) were derived by determining, by ELISAs, the percentage antigenicity of the conjugate relative to the native toxin and multiplying that value by 1000. One AU has the equivalent antigenicity 1 microgram (ug) of unattenuated native toxin.

I. Challenge procedures

The above immunized rats were challenged 4 to 6 days after the final booster immunization by instillation into a single 10-centimeter (cm) ligated loop of disal ileum for 18 hours of 0.1 ml of a broth culture containing $10^9$ viable organisms per ml of *E. coli* LT−/ST+ strain TX 452 (078:H12) of *E. coli* LT+/ST− strain PB258 (015:H−) as previously described [Klipstein et al., *J. Infect. Dis.* 147:318-326 (1983)) and Klipstein et al., *Infect. Immun.* 40:924-929 (1983)]. Each datum point was determined in 4 to 6 immunized rats, and the results reported are for the mean ± standard error of the mean (SEM) percentage reduced secretion in immunized rats as compared with the value in 5 similarly challenged unimmunized controls. Reduced secretion of less than 50 percent represented a significant (P less than 0.001) difference, as determined by Student's test for two independent means, between values in immunized and control animals.

J. Antitoxin response

Intestinal secretory IgA antitoxin titers to ST and B-subunit were determined by double sandwich ELISAs as described previously [Klipstein et al., *J. Infect. Dis.* 147:318-326 (1983)]. The reciprocal values for mean titers in each group are shown in FIGS. 3, 4 and 5 as numerals above or below data points.

VIII. DIAGNOSTIC ASSAYS SYSTEMS AND METHODS

The LTB polypeptides, composite LT/ST polypeptides and polymers containing a plurality of LTB polypeptide repeating units as well as antibodies and antibody combining sites (receptors) raised to the before described LTB polypeptides, composite LT/ST polypeptides and polymers, and methods of the present invention may also be used for diagnostic tests, such as immunoassays. Such diagnostic techniques include, for example, enzyme immune assay, enzyme multipled immunoassay technique (EMIT), enzyme-linked immunosorbent (ELISA), radio-immune assay (RIA), flourescence immune assay, either single or double antibody techniques, and other techniques in which either the receptor or the antigen is labeled with some detectable tag or indicating means. See generally Maggio, *Enzyme Immunoassay,* CRC Press, Cleveland, Ohio (1981); and Goldman, M., *Flourescent Antibody Methods,* Academic Press, New York, N.Y. (1980). Further specific examples of such assay methods, and systems useful in carrying out those methods are discussed hereinbelow.

A method for assaying for the presence of of native LT enterotoxin or its B-subunit in a body sample is contemplated herein. In a general method, a body sample such as a stool sample to be assayed is provided, and bacteria present therein are preferably cultured. The cultured bacterial sample or stool sample itself is admixed with receptor molecules that contain antibody combining sites induced by an LTB polypeptide-containing molecule of this invention such as one of the before described network polymers. The admixture is maintained for a predetermined period of time sufficient for the receptor molecules to immunoreact with enterotoxin present in the culture. The amount of that immunoreaction is then measured to determine whether enterotoxin molecules were present or absent in the assayed body sample.

An illustrative diagnostic system in kit form embodying one aspect the present invention that is useful for detecting LT enterotoxin present in a body sample contains receptor molecules of this invention induced by a polypeptide of this invention in one container. Exemplary of such receptors are antibodies, substantially whole antibodies, or antibody combining sites like Fab and $F(ab')_2$ antibody portions raised. This system also includes an indicating means for signaling the presence of an immunoreaction between the receptor and the antigen.

Typical indicating means include radioisotopes such as $^{125}I$ and $^{131}I$, enzymes such as alkaline phosphatase, horseradish peroxidase, beta-D-galactosidase and glucose oxidase, and fluorochrome dyes such as fluorescein and rhodamine. The indicating means may be linked directly to receptor of this invention. The indicating means may also be linked to a separate molecule such as to a second antibody, to an antibody combining site or to *Staphylococcus aureus* (*S. aureus*) protein A that reacts with (binds to) the receptor of this invention. Specific examples of separate molecule indicating means are $^{125}I$-labeled *S. aureus* protein A and peroxidase-coupled goat anti-rabbit antibodies.

The indicating means permits the immunoreaction product to be detected, and is packaged separately from the receptor when not linked directly to a receptor of this invention. When admixed with a bacterial culture sample, the receptor molecule immunoreacts with the LT enterotoxin to form an immunoreactant, and the indicating means present then signals the formation of immunoreaction product.

One embodiment of an LT enterotoxin diagnostic method is an immunoflourescent assay. In such an assay a bacterial cell culture smear is fixed to a plain microscope slide as a solid support. An aliquot of (receptors) antibodies raised in accordance with this invention, e.g., raised in rabbits, is contacted with the slide using well-known techniques. The receptors and bacterial cells are maintained in contact for a time period sufficient for the receptors to immunoreact with LT.

After rinsing away any un-immunoreacted receptors of this invention, any non-specific binding sites on the slide are typically blocked with a protein such as bovine serum albumin (BSA), if desired. A second reagent (an amplifying reagent) such as complement, or anti-immunoglobulin antibodies, e.g., guinea pig complement, may then be admixed and maintained in contact with the receptor-bound cells for a time sufficient for a reaction to occur (incubated).

After this second incubation, any unreacted of the amplifying reagent is removed as by rinsing leaving amplifying reagent bound to the first-named antibodies on the assay slide. A third reagent (indicating means), e.g., an antibody, like goat anti-guinea pig complement, is then contacted with the slide and its bound materials, and is maintained in contact for a time period sufficient for a reaction to take place with bound amplifying reagent (incubated). The third reagent is labeled by being linked to a flourochrome dye such as by reaction with fluorescein isothiocyanate (FITC), rhodamine B isothiocyanate (RITC), tetramethylrhodamine isothiocyanate (TRITC), 4, 4'-diisothiocyanostilbene-2,2'-disulfonic acid (DIDS), and the like as are well known in the art.

Any unreacted third reagent is rinsed off after this third incubation, leaving any flourochrome-labeled goat-antiguinea pig complement antibodies that bind to the complement on the slide. The presence of the fluorochrome dye-labeled third reagent may be detected using flourescence microscopy and thereby signal the presence of infection by an LT-producing strain of *E. coli.*

This assay may also be carried out without using the second and/or third reagent. Here, anti-LT receptors of this invention are bonded directly to a flourochrome dye and that indicating means-containing receptor is utilized directly.

A preferred diagnostic system, preferably in kit form, useful for carrying out the above assay method includes, in separate packages, (a) receptors (antibodies) of this invention that immunoreact with the native LT endotoxin (b) a second, amplifying reagent such as complement, like guinea pig complement, anti-immunogloulin antibodies or *S. aureus* protein A that reacts with the receptor, and (c) an indicating means that (i) may be linked directly to the amplifying means, (ii) may be a portion of a separate molecule such as an antibody or antibody-portion that reacts with the amplifying reagent, or (iii) may be linked directly to the anti-LT receptor, in which case, the kit need contain only a single immuno-reactive reagent. The indicating means indirectly signals the immunoreaction of the receptor molecule and an LT endotoxin, preferably through the mediation of the amplifying reagent.

Receptor molecules and separate indicating means of any diagnostic system described herein, as well as the above-described amplifying reagant, may be provided in solution, as a liquid dispersion or as a substantially dry powder, e.g., in lyophilized form. Where the indicating means is a separate molecule from the amplifying reagent, it is preferred that the indicating means be packaged separately. Where the indicating means is an enzyme, the enzyme's substrate may also be provided in a separate package of the system. A solid support such as the before-described microscope slide, one or more buffers and acetone may also be included as separately packaged elements in this diagnostic assay system.

The packages and containers discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

The use of whole, intact, biologically active antibodies is not necessary in many diagnostic systems such as the immunoflourescent assay described above. Rather, only the immunologically active, idiotype-containing, antigen binding and recognition receptor site; i.e., the antibody combining site, of the antibody molecule may be used. Examples of such antibody combining sites are those known in the art as Fab and $F(ab')_2$ antibody portions that are prepared by proteolysis using papain and pepsin, respectively, as is well known in the art.

Another diagnostic embodiment of this invention is particularly useful in competition assays, and this system, preferably in kit form, includes a first reagent and a second reagent in separate containers. Buffer salts in solid or liquid form, a microtiter plate, indicating means substrate and the like may also be included in their own containers.

A first reagent comprises an antigenic LTB polypeptide of this invention such as a network polymer containing composite LT/ST polypeptide repeating units as the antigen. The second reagent comprises receptors such as antibodies that immunoreact with the native LT B-subunit such as those discussed hereinbefore. A means for indicating the presence of an immunoreacion between the antigen and receptors is signalled by further, anti-receptor, receptors linked to a tag such as a radioactive element like $^{125}I$, a fluorescent dye like fluorescein or an enzyme like peroxidase. The indicating means is included either in a separate container as in peroxidase-linked goat anti-rabbit antibodies with another separate container for its substrate (e.g., o-phenylenediamine), or may be a part of the second reagent as where a radioactive element is bonded to the receptor molecules. The indicating means can also be separately supplied.

Admixture of predetermined amounts of the first and second reagents in the presence of a predetermined amount of a sample to be assayed such as a stool sample or a bacterial culture from a stool sample provides an amount of immunoreaction signalled by the indicating means. The amount of the immunoreaction is different from a known amount of immunoreaction when the enterotoxin or its B-subunit is present in the assayed sample.

In usual practice, an LTB polypeptide-containing antigen as a first reagent is bound to a solid support such as the walls of a microtiter plate or a nitrocellulose dip stick. Sites of non-specific binding on the solid support are bound by an unrelated protein such as BSA using well known techniques.

Predetermined amounts of the bacterial culture and second reagent are admixed in an aqueous medium. That admixture is maintained for a time period sufficient for the second reagent to immunoreact with LT endotoxin that may be present.

Thereafter, the solid support-bound first reagent and the bacterial culture-and second reagent-containing aqueous medium are admixed to form a solid/liquid phase admixture. That admixture is maintained for a time sufficient for second reagent present in the liquid phase to immunoreact with the solid phase-bound first reagent.

The solid and liquid phases are thereafter separated to provide a solid phase-bound immunoreactant. The amount of solid phase-bound immunoreactant is then measured and that amount is compared to an amount of immunoreaction that occurs when a known amount of LT enterotoxin is assayed in a similar manner.

The use of whole, intact, biologically active antibodies is again not necessary in many diagnostic systems such as the competition assay discussed immediately above. Rather, only the biologically active idiotype-containing amide portion of the antibody molecule that binds to the antigenic LTB polypeptide may be needed, as discussed hereinbefore.

The foregoing is intended as illustrative of the present invention but not limiting. Numerous variations and modifications may be effected without departing from the true spirit and scope of the novel concepts of the invention.

What is claimed is:

1. A synthetic polypeptide containing about 10 to about 35 amino acid residues corresponding in sequence to about position 35 to about position 95 from the amino-terminus of the B-subunit of the heat-labile enterotoxin of *Escherichia coli,* wherein said position numbers include the 21 residue signal polypeptide of said B-subunit.

2. The synthetic polypeptide according to claim 1 wherein said polypeptide contains about 15 to 30 amino acid residues corresponding in sequence to about position 55 to about position 85 of said B-subunit.

3. The synthetic polypeptide according to claim 1 wherein said polypeptide contains about 20 to about 25 amino acid residues corresponding in sequence to about position 60 to about position 85 of said B-subunit.

4. A synthetic, composite polypeptide containing about 25 to about 55 amino acid residues, said composite polypeptide comprising two amino acid residue sequences bonded together by a peptide bond, said two sequences being (a) a sequence of amino acid residues corresponding to at least the carboxy-terminal 14 residues of a heat-stable enterotoxin of *Escherichia coli* and (b) a sequence of amino acid residues correpsonding to residue positions about 35 to 95 from the amino-terminus of the B-subunit of the heat-labile enterotoxin of *Escherichia coli,* wherein said position numbers include the 21 residue signal polypeptide of said B-subunit.

5. The composite polypeptide according to claim 4 wherein said two sequences are bonded together by a peptide bond formed between the amino-terminal residue of said heat-stable enterotoxin sequence and the carboxy-terminal residue of said heat-labile enterotoxin B-subunit sequence.

6. The composite polypeptide according to claim 5, written from left to right and in the direction from amino-terminus to carboxy-terminus, corresponding to the formula MetValIleIleThrPheMet(Lys)SerGlyGlu
(Ala)ThrPheGlnValGluValProGlySerGln-
HisIleAspSerGlnLys
AsnThrPheTyrCysCysGluLeuCysCysTyr(Asn)
ProAlaCysAlaGlyCysAsn(Tyr)

wherein the amino acid residues in parentheses are each an alternative to the immediately preceding amino acid residue in the sequence of the formula.

7. A synthetic composite polypeptide, written from left to right and in the direction from amino-terminus to carboxy-terminus, corresponding to the formula:

$$(X)_n\text{-}(A)_o\text{-}(Z)_r\text{-}B\text{-}(Z)_s\text{-}(A)_p(Y)_m$$

wherein

X, Y and Z when present, are additional amino acid residues that are
(a) selected from the group consisting of a Lys and an Arg residue, or
(b) selected from the group consisting of an Asp and a Glu residue;

"n" and "m" are integers having a value of zero, 1,2,3 or 4, such that the respective X and Y are absent when either or both of "n" and "m" have a value of zero, while the respective X and Y residues are present when either or both of "n" and "m" have a value of other than zero, with the average number of X and Y residues present per polypeptide being equal to the values of X and Y, respectively;

"r" and "s" are integers having a value of zero, 1 or 2, such that the respective Z is absent when either or both of "r" and "s" have a value of zero, while the respective Z is present when "r" and "s" are not zero, the average number of Z residues per composite polypeptide molecule being equal to the value of "r" or "s", with the proviso that when either of "r" or "s" is greater than zero, the other of "r" or "s" is zero and the respective Z whose "r" or "s" is zero is absent;

"o" and "p" are integers having the value of zero or 1 so that the corresponding A is absent when either of "o" and "p" have a value of zero, with the proviso that "o" and "p" may not both have the same value;

A is a polypeptide containing about 10 to about 35 amino acid residues corresponding in sequence to the amino acid residue sequence of about position 35 to about position 95 from the amino-terminus of the B-subunit of the heat-labile enterotoxin of *Escherichia coli,* wherein the position numbers include the 21 residue signal polypeptide of the B-subunit; and B is a polypeptide containing up to 18 amino acid residues corresponding in sequence to at least the carboxy-terminal 14 residues of the heat-stable enterotoxin of *Escherichia coli.*

8. The polypeptide according to claim 7 wherein:

"n" is 2;

X is Lys;

"o" is 1;

"r", "s", "p" and "m" are zero;

A is a polypeptide, written from left to right and in the direction from amino-terminus to carboxy-terminus, that corresponds to the formula:

MetValIleIleThrPheMet(Lys)SerGlyGlu(Ala)Thr-Phe GlnValGluValProGlySerGlnHisIleAsp-SerGlnLys; and B is a polypeptide, written from left to right and in the direciton from amino-terminus to carboxy-terminus, that corresponds to the formula:

AsnThrPheTyrCysCysGluLeuCysCysTyr(Asn)-ProAla CysAlaGlyCysAsn(Tyr), wherein the parenthesized amino acid residues in each of said polypeptides is an alternative to the immediately preceding amino acid residue in said sequences.

9. A polymer comprising a plurality of polypeptide repeating units, said polypeptide repeating units containing about 10 to about 35 amino acid residues corresponding in sequence to the amino acid residue sequence of about position 35 to about position 95 from the amino-terminus of the B-subunit of the heat-labile enterotoxin of *Escherichia coli,* wherein said position numbers include the 21 residue signal peptide of said B-subunit.

10. The polymer according to claim 9 wherein said repeating units are bonded together by cystine disulfide bonds formed by oxidation of Cys residues present at both the amino-terminus and the carboxy-terminus of said repeating unit polypeptides prior to oxidation.

11. The polymer according to claim 10 wherein said polymer is a linear homopolymer.

12. The polymer according to claim 9 wherein said polymer is a random network copolymer that further comprises a plurality of second polypeptide repeating units, written from left to right and in the direction from amino-terminus to carboxy-terminus, including a polypeptide sequence corresponding to the formula

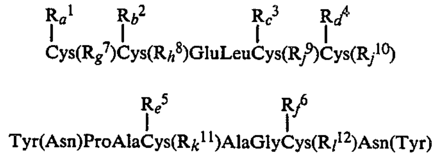

wherein the Asn and Tyr amino acid residues in parentheses are each an alternative to the immediately preceding amino acid residue in the sequence of the formula;

a, b, c, d, e and f and g, h, i, j, k and l are integers each having a value of zero or one, with the proviso that if the value of any of a-f or g-l is zero, the corresponding $R_a^1$, $R_b^2$, $R_c^3$, $R_c^4$, $R_e^5$ or $R_f^6$ group or $R_g^7$, $R_h^8$, $R_i^9$, $R_j^{10}$, $R_k^{11}$ or $R_l^{12}$ group is absent, and when an $R_{a\text{-}f}^{1\text{-}6}$-group is absent the sulfur atom of the Cys residue having an absent $R_{a\text{-}f}^{1\text{-}6}$-group forms a cystine disulfide bond, while if the value of any one of a-f or g-l is one, the corresponding $R_{a\text{-}f}^{1\text{-}6}$- or $R_{g\text{-}l}^{7\text{-}12}$-group is present;

the $R_{a\text{-}f}^{1\text{-}6}$-groups when taken individually, are the same or different moieties bonded to the sulfur atoms of the Cys residue and are selected from the group consisting of hydrogen, an alkyl group containing 1 to about 4 carbon atoms, and a substituted alkyl group containing 2 to about 4 carbon atoms;

$R_{g\text{-}l}^{7\text{-}12}$ are the same or different alternative amino acid residues to each immediately preceding Cys residue shown in the formula, and are selected from the group of amino acid residues having neutral a side chain;

at least four of a-f and four of g-l are zero;

said first-named and said second polypeptide repeating units being present in said copolymer at a molar ratio of 1:10 to 10:1; and said first-named and said second polypeptide repeating units are bonded together by cystine disulfide bonds formed by oxidation of Cys residues present in each of said repeating units.

13. The polymer according to claim 9 wherein said polymer is a random network copolymer that further comprises a plurality of second polypeptide repeating units, written from left to right and in the direction from amino-terminus to carboxy-terminus, corresponding to the formula $$\begin{array}{l} \qquad\qquad\qquad R_a^1 \quad\; R_b^2 \qquad\qquad\quad R_c^3 \\ \qquad\qquad\qquad | \qquad\;\; | \qquad\qquad\quad\;\; | \\ \text{AsnThrPheTyrCys}(R_g^7)\text{Cys}(R_h^8)\text{GluLeuCys}(R_i^9) \end{array}$$

$$\begin{array}{l} \text{Cys}(R_j^{10})\text{Tyr(Asn)ProAlaCys}(R_k^{11})\text{AlaGlyCys}(R_l^{12})\text{Asn(Tyr)} \\ | \qquad\qquad\qquad\qquad\quad | \qquad\qquad\quad | \\ R_d^4 \qquad\qquad\qquad\qquad\; R_e^5 \qquad\qquad R_f^6 \end{array}$$

wherein the Asn and Tyr amino acid residues in parentheses are each an alternative to the immediately preceding amino acid residue in the sequence of the formula;

a, b, c, d, e and f and g, h, i, j, k and l are integers each having a value of zero or one, with the proviso that if the value of any of a-f or g-l is zero, the corresponding $R_a^1$, $R_b^2$, $R_c^3$, $R_d^4$, $R_e^5$ or $R_f^6$ group or $R_g^7$, $R_h^8$, $R_i^9$, $R_j^{10}$, $R_k^{11}$ or $R_l^{12}$ group is absent, and when an $R_{a\text{-}f}^{1\text{-}6}$-group is absent the sulfur atom of the Cys residue having an absent $R_{a\text{-}f}^{1\text{-}6}$-group forms a cystine disulfide bond, while if the value of any one of a-f or g-l is one, the corresponding $R_{a\text{-}f}^{1\text{-}6}$- or $R_{g\text{-}l}^{7\text{-}12}$-group is present;

the $R_{a\text{-}f}^{1\text{-}6}$-groups when taken individually, are the same or different moieties bonded to the sulfur atom of the Cys residue and are selected from the group consisting of hydrogen, an alkyl group containing 1 to about 4 carbon atoms, and a substituted alkyl group containing 2 to about 4 carbon atoms;

$R_{g\text{-}l}^{7\text{-}12}$ are the same or different alternative amino acid residues to each immediately preceding Cys residue shown in the formula, and are selected from the group of amino acid residues having a neutral side chain;

at least four of a-f and four of g-l are zero;

said first-named and said second polypeptide repeating units are present in said copolymer at a molar ratio of 1:10 to 10:1; and said first-named and said second polypeptide repeating units being bonded together by cystine disulfide bonds formed by oxidation of Cys residues present in each of said repeating units.

14. The polymer according to claim 13 wherein a-f and g-l are zero.

15. The polymer according to claim 9 wherein said polymer is a network polymer containing a plurality of repeating units, said repeatng units including said about 10 to about 35 amino acid residue polypeptide sequence peptide-bonded to a second polypeptide to form a composite polypeptide repeating unit containing about 25 to about 55 amino acid residues, said composite polypeptide, written from left to right and in the direction of amino-terminus to carboxy-terminus, corresponding to the formula $$(X)_n\text{-}(A)_o\text{-}(Z)_r\text{-}B\text{-}(Z)_s(A)_p\text{-}(Y)_m$$

wherein:

X, Y, and Z, when present, are amino acid residues that are (a) selected from the group consisting of a Lys and an Arg residue, or (b) selected from the group consisting of an Asp and a Glu residue;

"n" and "m" are integers having a value of zero, 1,2,3 or 4, such that the respective X and Y are absent when either or both of "n" and "m" have a value of zero, while the respective X and Y residues are present when either or both of "n" and "m" have a value of other than zero, with the average number of X and Y residues present per polypeptide being equal to the values of X and Y, respectively;

"r" and "s" are integers having a value of zero, 1 or 2, such that the respective Z is absent when either or both of "r" and "s" have a value of zero, while the respective Z is present when "r" and "s" are present, the average number of Z residues per composite polypeptide repeating unit being equal to the value of "r" or "s", with the proviso that when either of "r" or "s" is greater than zero, the other of "r" or "s" is zero and the respective Z whose "r" or "s" is zero is absent;

"o" and "p" are integers having the value of zero or 1 so that the corresponding A is absent when either of "o" and "p" have a value of zero, with the proviso that "o" and "p" may not both have the same value;

A is said first-named about 10 to about 35 amino acid residue polypeptide sequence; and B is said second polypeptide that includes an amino acid sequence, written from left to right and in the direciton from amino-terminus to carboxy-terminus, corresponding to the formula $$\begin{array}{l} R_a^1 \quad\;\; R_b^2 \qquad\qquad\qquad R_c^3 \quad\; R_d^4 \\ | \qquad\;\; | \qquad\qquad\qquad\;\; | \qquad | \\ \text{Cys}(R_g^7)\text{Cys}(R_h^8)\text{GluLeuCys}(R_i^9)\text{Cys}(R_j^{10}) \end{array}$$

-continued $$\begin{matrix} & & R_e^5 & & R_f^6 & \\ \text{Tyr(Asn)ProAla} & & \text{Cys}(R_k^{11}) & \text{AlaGly} & \text{Cys}(R_l^{12}) & \text{Asn(Tyr)} \end{matrix}$$

wherein the Asn and Tyr amino acid residues in parentheses are each an alternative to the immediately preceding amino acid residue in the sequence of the formula;

a, b, c, d, e and f and g, h, i, j, k and l are integers each having a value of zero or one, with the proviso that if the value of any of a-f or g-l is zero, the corresponding $R_a^1$, $R_b^2$, $R_c^3$, $R_d^4$, $R_e^5$ or $R_f^6$ group or $R_g^7$, $R_h^8$, $R_i^9$, $R_j^{10}$, $R_k^{11}$ or $R_l^{12}$ group is absent, and when an $R_{a\text{-}f}^{1\text{-}6}$-group is absent the sulfur atom of the Cys residue having an absent $R_{a\text{-}f}^{1\text{-}6}$-group forms a cystine disulfide bond, while if the value of any one of a-f or g-l is one, the corresponding $R_{a\text{-}f}^{1\text{-}6}$- or $R_{g\text{-}l}^{7\text{-}12}$-group is present;

the $R_{a\text{-}f}^{1\text{-}6}$-groups when taken individually, are the same or different moieties bonded to the sulfur atom of the Cys residue and are selected from the group consiting of hydrogen, an alkyl group containing 1 to about 4 carbon atoms, and a substituted alkyl group containing 2 to about 4 carbon atoms;

$R_{g\text{-}l}^{7\text{-}12}$ are the same or different alternative amino acid residues to each immediately preceding Cys residue shown in the formula, and are selected from the group of amino acid residues having a neutral side chain;

at least four of a-f and four of g-l are zero; and said composite polypeptide repeating units are bonded together by cystine disulfide bonds formed by oxidation of Cys residues present in said repeating units.

16. The polymer according to claim 15 wherein said composite polypetpide repeating unit, written from left to right and in the direction from amino-terminus to carboxy-terminus, is selected from the group of polypeptides consisting of:

(a) MetValIleIleThrPheMetSerGlyGluThrPheGln ValGluValProGlySerGlnHisIleAspSerGlnLysAsnThrPheTyrCys CysGluLeuCysCysTyrProAlaCysAlaGlyCysAsn, (b) LysLysMetValIleIleThrPheMetSerGlyGluThr PheGlnValGluValProGlySerGlnHisIleAspSerGlnLysValGluVal ProGlySerGlnHisIleAspSerGlnLysAsnThrPheTyrCysCysGluLeu CysCysTyrProAlaCysAlaGlyCysAsn, (c) AsnThrGlnIleTyrThrIleAsnAspLysIle LeuSerTyrThrGluSerMetAlaGlyLysAsnThrPheTyrCysCysGluLeu CysCysTyrProAlaCysAlaGlyCysAsn, (d) GlnIleTyrThrIleAsnAspLysIleLeuSerTyrThr GluSerMetAlaGlyLysArgGluMetValIleIleThrPheMetSerGlyGlu ThrPheGlnValGluValProGlycAsnThrPheTyrCysCysGluLeuCysCys TyrProAlaCysAlaGlyCysAsn, (e) MetSerGlyGluThrPheGlnValGluValProGlyAsn ThrPheTyrCysCysGluLeuCysCysTyrProAlaCysAlaGlyCysAsn, (f) PheMetSerGlyGluThrPheGlnValGluValProGly SerGlnHisIleAspSerGlnLysAsnThrPheTyrCysCysGluLeuCysCys TyrProAlaCysAlaGlyCysAsn, (g) PheGlnValGluValProGlySerGlnHisIleAspSer GlnLysAsnThrPheTyrCysCysGluLeuCysCysTyrProAlaCysAlaGly CysAsn, (h) SerGlnHisIleAspSerGlnLysAsnThrPheTyrCys CysGluLeuCysCysTyrProAlaCysAlaGlyCysAsn, (i) TyrThrGluSerMetAlaGlyLysAsnThrPheTyrCys CysGluLeuCysCysTyrProAlaCysAlaGlyCysAsn, and (j) AsnThrPheTyrCysCysGluLeuCysCysTyrProAla CysAlaGlyCysAsnAsnThrGlnIleTyrThrIleAsnAspLysIleLeuSerTyrThrGluSerMetAlaGlyLys.

17. A network polymer comprising a plurality of polypeptide repeating units, said repeating units being bonded by interpolypeptide cystine bonds formed between the Cys residues of the repeating units, said repeating units, written from left to right and in the direction from amino-terminus to carboxy-terminus, individually corresponding to the formula:

$(X)_n$MetValIleIleThrPheMet(Lys)SerGlyGlu
(Ala)ThrPheGlnValGluValProGlySerGln-
HisIleAspSerGlnLys
AsnThrPheTyrCysCysGluLeuCysCysTyr(Asn)
ProAlaCysAlaGlyCysAsn(Tyr)$(Y)_m$ wherein X and Y, when present, are amino acid residues that are (a) both selected from the group consisting of a Lys and an Arg residue, or (b) both selected from the group consisting of an Asp and a Glu residue; and "n" and "m" are integers having the value of zero, 1, 2, 3 or 4, such that when either or both of "n" and "m" have a value of zero, the respective X and Y are absent, while when either or both of "n" and "m" have a value of other than zero, the respective X and Y residues are present, with the average number of X and Y residues present per polypeptide repeating unit being equal to the values of X and Y, respectively; and the amino acid residues in parentheses are each an alternative to the immediately preceding amino acid residue in the sequence of the formula.

18. The network polymer according to claim 17 wherein:

"n" is 2;

X is Lys; and

"m" is zero.

19. The network polymer according to claim 17 wherein:

"N" and "m" are both zero.

* * * * *